(12) United States Patent
Griffin

(10) Patent No.: US 12,251,112 B2
(45) Date of Patent: Mar. 18, 2025

(54) OCCLUSION DEVICE

(71) Applicant: Cerus Endovascular Limited, Fremont, CA (US)

(72) Inventor: Stephen Griffin, San Jose, CA (US)

(73) Assignee: Stryker Ireland Technology Ltd., Carrigtwohill County (IE)

( * ) Notice: Subject to any disclaimer, the term of this patent is extended or adjusted under 35 U.S.C. 154(b) by 0 days.

(21) Appl. No.: 18/481,326

(22) Filed: Oct. 5, 2023

(65) Prior Publication Data

US 2024/0032939 A1     Feb. 1, 2024

Related U.S. Application Data

(63) Continuation of application No. 16/640,142, filed as application No. PCT/EP2018/072576 on Aug. 21, 2018, now Pat. No. 11,812,971.

(Continued)

(51) Int. Cl.
*A61B 17/12*     (2006.01)
*A61B 90/00*     (2016.01)

(52) U.S. Cl.
CPC .. *A61B 17/12172* (2013.01); *A61B 17/12113* (2013.01); *A61B 2017/1205* (2013.01);
(Continued)

(58) Field of Classification Search
CPC ........ A61B 17/12172; A61B 17/12168; A61B 17/12113; A61B 2090/3966;
(Continued)

(56) References Cited

U.S. PATENT DOCUMENTS 2,849,002 A    8/1958   Oddo
3,480,017 A    11/1969   Shute
(Continued)

FOREIGN PATENT DOCUMENTS

CA     2946078     11/2015
CN     102940514     3/2013
(Continued)

OTHER PUBLICATIONS

US 9,034,010 B2, 05/2015, Amin (withdrawn)
(Continued)

*Primary Examiner* — Sarah A Long
*Assistant Examiner* — Raihan R Khandker
(74) *Attorney, Agent, or Firm* — McDonnell Boehnen Hulbert & Berghoff LLP

(57) ABSTRACT

Provided herein is an occlusion device comprising: (a) continuous mesh structure comprising a medial pinch point; (b) a resilient mesh disc-shaped body extending distally and outward from the medial pinch point; and (c) a compressible mesh carriage extending distally from the medial pinch point on an opposing side of the resilient mesh body of (b), wherein the compressible mesh carriage comprises a pinch point on each end of the carriage, wherein one of the pinch points is the medial pinch point of (a); wherein the continuous mesh structure has a first delivery shape and a second expandable deployed shape, and wherein the length (x) of the resilient mesh body is greater than the length (y) of the compressible mesh carriage in free air and in the deployed shape.

16 Claims, 3 Drawing Sheets

Related U.S. Application Data

(60) Provisional application No. 62/547,966, filed on Aug. 21, 2017.

(52) U.S. Cl.
CPC ............... *A61B 2017/12063* (2013.01); *A61B 2090/3966* (2016.02)

(58) Field of Classification Search
CPC .. A61B 2017/1205; A61B 2017/12063; A61B 2017/12054
See application file for complete search history.

(56) References Cited

U.S. PATENT DOCUMENTS

| | | | |
|---|---|---|---|
| 4,364,392 A | 12/1982 | Strother et al. |
| 4,395,806 A | 8/1983 | Wonder et al. |
| 4,545,367 A | 10/1985 | Tucci |
| 4,836,204 A | 6/1989 | Laudvmore et al. |
| 4,991,602 A | 2/1991 | Amplatz et al. |
| 5,002,556 A | 3/1991 | Ishida et al. |
| 5,025,060 A | 6/1991 | Yabuta et al. |
| 5,065,772 A | 11/1991 | Cox, Jr. |
| 5,067,489 A | 11/1991 | Lind |
| 5,122,136 A | 6/1992 | Guglielmi et al. |
| 5,192,301 A | 3/1993 | Kamiya et al. |
| 5,423,829 A | 6/1995 | Pham et al. |
| 5,496,277 A | 3/1996 | Temlin et al. |
| 5,624,449 A | 4/1997 | Pham et al. |
| 5,733,294 A | 3/1998 | Forber et al. |
| 5,891,128 A | 4/1999 | Gia et al. |
| 5,928,260 A | 7/1999 | Chin et al. |
| 6,007,573 A | 12/1999 | Wallace et al. |
| 6,024,756 A | 2/2000 | Pham |
| 6,080,191 A | 6/2000 | Thaler |
| 6,096,021 A | 8/2000 | Helm et al. |
| 6,113,609 A | 9/2000 | Adams |
| 6,123,714 A | 9/2000 | Gia et al. |
| 6,152,144 A | 11/2000 | Lesh et al. |
| 6,168,579 B1 | 1/2001 | Tsugita |
| 6,168,622 B1 | 1/2001 | Mazzocclli |
| 6,221,086 B1 | 4/2001 | Forber |
| 6,270,515 B1 | 8/2001 | Linden et al. |
| 6,315,787 B1 | 11/2001 | Tsugita et al. |
| 6,334,048 B1 | 12/2001 | Edvardsson et al. |
| 6,419,686 B1 | 7/2002 | McLeod et al. |
| 6,454,780 B1 | 9/2002 | Wallace |
| 6,463,317 B1 | 10/2002 | Kucharczyk et al. |
| 6,506,204 B2 | 1/2003 | Mazzocchi |
| 6,527,919 B1 | 3/2003 | Roth |
| 6,547,804 B2 | 4/2003 | Porter et al. |
| 6,551,303 B1 | 4/2003 | Tassel et al. |
| 6,569,190 B2 | 5/2003 | Vhalen, II et al. |
| 6,589,230 B2 | 7/2003 | Gia et al. |
| 6,589,256 B2 | 7/2003 | Forber |
| 6,605,102 B1 | 8/2003 | Mazzocchi et al. |
| 6,620,152 B2 | 9/2003 | Guglielmi |
| 6,663,068 B2 | 12/2003 | Huang |
| 6,669,719 B2 | 12/2003 | Wallace et al. |
| 6,669,721 B1 | 12/2003 | Bose et al. |
| 6,689,159 B2 | 2/2004 | Lau et al. |
| 6,780,196 B2 | 8/2004 | Chin et al. |
| 6,811,560 B2 | 11/2004 | Jones |
| 6,833,003 B2 | 12/2004 | Jones et al. |
| 6,855,154 B2 | 2/2005 | Abdel-Gawwad |
| 6,949,116 B2 | 9/2005 | Solymar et al. |
| 6,953,472 B2 | 10/2005 | Palmer |
| 7,044,134 B2 | 5/2006 | Khairkhahan et al. |
| 7,093,527 B2 | 8/2006 | Rapaport et al. |
| 7,128,073 B1 | 10/2006 | Burg et al. |
| 7,128,736 B1 | 10/2006 | Abrams et al. |
| 7,152,605 B2 | 12/2006 | Khairkhahan et al. |
| 7,195,636 B2 | 3/2007 | Avellanet et al. |
| 7,229,454 B2 | 6/2007 | Tran et al. |
| 7,229,461 B2 | 6/2007 | Chin et al. |
| 7,232,461 B2 | 6/2007 | Ramer |
| 7,306,622 B2 | 12/2007 | Jones |
| 7,371,249 B2 | 5/2008 | Douk et al. |
| 7,410,482 B2 | 8/2008 | Mumhev |
| 7,572,288 B2 | 8/2009 | Cox |
| 7,597,704 B2 | 10/2009 | Frazier et al. |
| 7,695,488 B2 | 4/2010 | Berenstein et al. |
| 7,713,264 B2 | 5/2010 | Murphy |
| 7,722,641 B2 | 5/2010 | Burg et al. |
| 7,744,652 B2 | 6/2010 | Morsi |
| 7,828,818 B2 | 11/2010 | Zang et al. |
| 7,892,254 B2 | 2/2011 | Klint |
| 8,034,061 B2 | 10/2011 | Amplatz et al. |
| 8,066,757 B2 | 11/2011 | Ferrera |
| 8,075,585 B2 | 12/2011 | Lee et al. |
| 8,080,032 B2 | 12/2011 | Bure et al. |
| 8,088,140 B2 | 1/2012 | Ferrera |
| 8,142,456 B2 | 3/2012 | Rosaueta et al. |
| 8,221,483 B2 | 7/2012 | Ford et al. |
| 8,252,040 B2 | 8/2012 | Cox |
| 8,261,648 B1 | 9/2012 | Marchand et al. |
| 8,262,692 B2 | 9/2012 | Rudakov |
| 8,267,923 B2 | 9/2012 | Murphy |
| 8,361,106 B2 | 1/2013 | Solar et al. |
| 8,361,138 B2 | 1/2013 | Adams |
| 8,372,114 B2 | 2/2013 | Hines |
| 8,398,671 B2 | 3/2013 | Chen |
| 8,430,012 B1 | 4/2013 | Marchand et al. |
| 8,454,633 B2 | 6/2013 | Amolatz et al. |
| 8,470,013 B2 | 6/2013 | Duggal et al. |
| 8,500,751 B2 | 8/2013 | Rudakov et al. |
| 8,523,897 B2 | 9/2013 | van der Burg et al. |
| 8,535,343 B2 | 9/2013 | Burg et al. |
| 8,454,514 B2 | 10/2013 | Ferrera |
| 8,562,667 B2 | 10/2013 | Cox |
| 8,574,262 B2 | 11/2013 | Ferrera |
| 8,585,713 B2 | 11/2013 | Ferrera |
| 8,597,320 B2 | 12/2013 | Sepetka |
| 8,663,273 B2 | 3/2014 | Khairkhahan |
| 8,696,701 B2 | 4/2014 | Becking |
| 8,715,312 B2 | 5/2014 | Burke |
| 8,715,316 B1 | 5/2014 | Janardhan et al. |
| 8,747,453 B2 | 6/2014 | Amplatz |
| 8,771,294 B2 | 7/2014 | Sepetka |
| 8,834,519 B2 | 9/2014 | Vanderburg |
| 8,926,680 B2 | 1/2015 | Ferrera |
| 8,945,172 B2 | 2/2015 | Ferrera |
| 9,034,054 B2 | 5/2015 | Gerberding |
| 9,039,724 B2 | 5/2015 | Amplatz et al. |
| 9,060,077 B2 | 6/2015 | Sayama |
| 9,060,777 B1 | 6/2015 | Wallace |
| 9,078,658 B2 | 7/2015 | Hewitt |
| 9,107,670 B2 | 8/2015 | Hannes |
| 9,138,213 B2 | 9/2015 | Amin |
| 9,161,758 B2 | 10/2015 | Figulla |
| 9,168,043 B2 | 10/2015 | Vanderburg |
| 9,179,918 B2 | 11/2015 | Levy |
| 9,186,487 B2 | 11/2015 | Dumbl et al. |
| 9,198,668 B2 | 12/2015 | Theobald |
| 9,198,670 B2 | 12/2015 | Hewitt |
| 9,198,687 B2 | 12/2015 | Fulkerson |
| 9,220,522 B2 | 12/2015 | Fulkerson |
| 9,259,337 B2 | 2/2016 | Cox |
| 9,271,736 B2 | 3/2016 | Heipl |
| 9,295,473 B2 | 3/2016 | Hewitt |
| 9,307,998 B2 | 4/2016 | Chin |
| 9,314,326 B2 | 4/2016 | Wallace |
| 9,387,098 B2 | 7/2016 | Ferrera |
| 9,474,517 B2 | 10/2016 | Amin |
| 9,492,174 B2 | 11/2016 | Hewitt |
| 9,498,604 B2 | 11/2016 | Dubrul |
| 9,532,772 B2 | 1/2017 | Moszner |
| 9,539,122 B2 | 1/2017 | Burke |
| 9,545,300 B2 | 1/2017 | Cully |
| 9,572,698 B2 | 2/2017 | Franano |
| 9,597,087 B2 | 3/2017 | Marchand |
| 9,622,770 B2 | 4/2017 | Trapp |
| 9,629,635 B2 | 4/2017 | Hewitt |
| 9,795,400 B2 | 10/2017 | Davidson |

(56) References Cited

U.S. PATENT DOCUMENTS

| | | |
|---|---|---|
| 9,826,980 B2 | 11/2017 | Figulla |
| 9,839,430 B2 | 12/2017 | Willems |
| 9,861,467 B2 | 1/2018 | Cully |
| 9,877,726 B2 | 1/2018 | Lin |
| 9,918,720 B2 | 3/2018 | Marchand |
| 9,943,299 B2 | 4/2018 | Khairkhahan |
| 9,955,976 B2 | 5/2018 | Hewitt |
| 9,962,146 B2 | 5/2018 | Hebert |
| 9,980,733 B2 | 5/2018 | Badruddin |
| 10,028,745 B2 | 7/2018 | Morsi |
| 10,028,747 B2 | 7/2018 | Connor |
| 10,076,399 B2 | 9/2018 | Davidson |
| 10,123,803 B2 | 11/2018 | Ferrera et al. |
| 10,130,372 B2 | 11/2018 | Griffin |
| 10,136,896 B2 | 11/2018 | Hewitt et al. |
| 10,159,490 B2 | 12/2018 | Wallace et al. |
| 10,231,722 B2 | 3/2019 | Hebert et al. |
| 10,238,393 B2 | 3/2019 | Marchand et al. |
| 10,265,075 B2 | 4/2019 | Porter et al. |
| 10,278,705 B2 | 5/2019 | Amin et al. |
| 10,285,678 B2 | 5/2019 | Hebert et al. |
| 10,285,679 B2 | 5/2019 | Hebert et al. |
| 10,285,711 B2 | 5/2019 | Griffin |
| 10,299,775 B2 | 5/2019 | Hebert et al. |
| 10,342,546 B2 | 7/2019 | Sepetka et al. |
| 10,383,635 B2 | 8/2019 | Wallace et al. |
| 10,398,441 B2 | 9/2019 | Warner et al. |
| 10,398,444 B2 | 9/2019 | Morsi |
| 10,433,851 B2 | 10/2019 | Adams et al. |
| 10,478,194 B2 | 11/2019 | Rhee et al. |
| 10,499,939 B2 | 12/2019 | Davidson |
| 10,537,451 B2 | 1/2020 | Franano et al. |
| 10,543,015 B2 | 1/2020 | Walzman |
| 10,543,115 B2 | 1/2020 | Franano et al. |
| 10,548,607 B2 | 2/2020 | Walzman |
| 10,561,441 B2 | 2/2020 | Cole et al. |
| 10,603,070 B2 | 3/2020 | Walzman |
| 10,610,231 B2 | 4/2020 | Marchand et al. |
| 10,617,428 B2 | 4/2020 | Walzman |
| 10,653,403 B2 | 5/2020 | Hebert et al. |
| 10,716,549 B2 | 7/2020 | Keillor |
| 10,716,573 B2 | 7/2020 | Connor |
| 10,716,574 B2 | 7/2020 | Lorenzo et al. |
| 10,729,447 B2 | 8/2020 | Shimizu et al. |
| 10,743,852 B2 | 8/2020 | Koszner et al. |
| 10,743,884 B2 | 8/2020 | Lorenzo |
| 10,751,065 B2 | 8/2020 | Soto Del Valle et al. |
| 10,751,066 B2 | 8/2020 | Lorenzo |
| 10,772,747 B2 | 9/2020 | Fischer et al. |
| 10,808,341 B2 | 10/2020 | Konne |
| 10,813,645 B2 | 10/2020 | Hewitt et al. |
| 10,835,257 B2 | 11/2020 | Ferrera et al. |
| 10,856,879 B2 | 12/2020 | Badruddin et al. |
| 10,856,880 B1 | 12/2020 | Badruddin et al. |
| 10,869,672 B2 | 12/2020 | Griffin |
| 10,881,413 B2 | 1/2021 | Merrit et al. |
| 10,888,333 B2 | 1/2021 | Kealey et al. |
| 10,905,430 B2 | 2/2021 | Lorenzo et al. |
| 10,925,612 B2 | 2/2021 | Wallace et al. |
| 10,939,914 B2 | 3/2021 | Hewitt et al. |
| 10,939,915 B2 | 3/2021 | Gorochow et al. |
| 10,952,739 B2 | 3/2021 | Plaza et al. |
| 10,959,735 B2 | 3/2021 | Morsi |
| 10,980,545 B2 | 4/2021 | Bowman et al. |
| 11,006,940 B2 | 5/2021 | Herbert et al. |
| 11,033,277 B2 | 6/2021 | Wolfe et al. |
| 11,045,177 B2 | 6/2021 | Walzman |
| 11,045,203 B2 | 6/2021 | Sepetka et al. |
| 11,058,430 B2 | 7/2021 | Gorochow et al. |
| 11,058,431 B2 | 7/2021 | Pereira et al. |
| 11,076,860 B2 | 8/2021 | Lorenzo |
| 11,076,861 B2 | 8/2021 | Gorochow et al. |
| 11,090,078 B2 | 8/2021 | Walzman |
| 11,090,176 B2 | 8/2021 | Franano et al. |
| 11,123,077 B2 | 9/2021 | Lorenzo et al. |
| 11,134,933 B2 | 10/2021 | Amplatz et al. |
| 11,154,302 B2 | 10/2021 | Lorenzo |
| 11,166,731 B2 | 11/2021 | Wolfe et al. |
| 11,179,159 B2 | 11/2021 | Cox et al. |
| 11,185,335 B2 | 11/2021 | Badruddin et al. |
| 11,202,636 B2 | 12/2021 | Zaidat et al. |
| 11,241,223 B2 | 2/2022 | Herbert et al. |
| 11,253,261 B2 | 2/2022 | Jayaraman |
| 11,266,414 B2 | 3/2022 | Fulton, III |
| 11,284,901 B2 | 9/2022 | Griffin |
| 2001/0041900 A1 | 11/2001 | Callister |
| 2002/0082638 A1 | 6/2002 | Porter et al. |
| 2002/0143349 A1 | 10/2002 | Gifford, II et al. |
| 2002/0169473 A1 | 11/2002 | Seietka |
| 2002/0188314 A1 | 12/2002 | Anderson et al. |
| 2003/0055451 A1 | 3/2003 | Jones et al. |
| 2003/0120337 A1 | 6/2003 | Tassel et al. |
| 2003/0171739 A1 | 9/2003 | Murphy et al. |
| 2003/0176884 A1 | 9/2003 | Berrada |
| 2003/0181927 A1 | 9/2003 | Wallace |
| 2003/0195553 A1 | 10/2003 | Wallace et al. |
| 2003/0220667 A1 | 11/2003 | Van Der Burg |
| 2004/0034366 A1 | 2/2004 | Burg et al. |
| 2004/0044391 A1 | 3/2004 | Porter |
| 2004/0087998 A1 | 5/2004 | Lee et al. |
| 2004/0098027 A1 | 5/2004 | Teoh et al. |
| 2004/0127935 A1 | 7/2004 | Tassel et al. |
| 2004/0133222 A1 | 8/2004 | Tran et al. |
| 2004/0167597 A1 | 8/2004 | Costantino |
| 2004/0172056 A1 | 9/2004 | Guterman |
| 2004/0181253 A1 | 9/2004 | Sepetka |
| 2004/0193246 A1 | 9/2004 | Ferrera |
| 2004/0254594 A1 | 12/2004 | Alfaro |
| 2004/0260332 A1 | 12/2004 | Dubrul |
| 2005/0021016 A1 | 1/2005 | Malecki et al. |
| 2005/0119684 A1 | 6/2005 | Gutterman |
| 2005/0251200 A1 | 11/2005 | Porter |
| 2006/0052816 A1 | 3/2006 | Bates et al. |
| 2006/0058735 A1 | 3/2006 | Lesh |
| 2006/0064151 A1 | 3/2006 | Guterman |
| 2006/0116709 A1 | 6/2006 | Sepetka |
| 2006/0116713 A1 | 6/2006 | Sepetka |
| 2006/0155323 A1 | 7/2006 | Porter et al. |
| 2006/0155367 A1 | 7/2006 | Hines |
| 2006/0167494 A1 | 7/2006 | Suddaby |
| 2006/0206199 A1 | 9/2006 | Churchwell et al. |
| 2007/0043391 A1 | 2/2007 | Moszner et al. |
| 2007/0106311 A1 | 5/2007 | Wallace et al. |
| 2007/0150045 A1 | 6/2007 | Ferrera |
| 2007/0173928 A1 | 7/2007 | Morsi |
| 2007/0198075 A1 | 8/2007 | Levy |
| 2007/0203567 A1 | 8/2007 | Levy |
| 2007/0208376 A1 | 9/2007 | Meng |
| 2007/0225760 A1 | 9/2007 | Moszner |
| 2007/0270902 A1 | 11/2007 | Slazas |
| 2007/0288083 A1 | 12/2007 | Hines |
| 2008/0045995 A1 | 2/2008 | Guterman |
| 2008/0097401 A1 | 4/2008 | Trapp |
| 2008/0097495 A1 | 4/2008 | Feller, III et al. |
| 2008/0147100 A1 | 6/2008 | Wallace |
| 2008/0221600 A1 | 9/2008 | Dieck et al. |
| 2009/0082803 A1 | 3/2009 | Adams |
| 2009/0099647 A1 | 4/2009 | Glimsdale et al. |
| 2009/0192455 A1 | 7/2009 | Ferrera |
| 2009/0209855 A1 | 8/2009 | Drilling et al. |
| 2009/0228029 A1 | 9/2009 | Lee |
| 2009/0281557 A1 | 11/2009 | Sander et al. |
| 2009/0297582 A1 | 12/2009 | Meyer |
| 2009/0318941 A1 | 12/2009 | Sepetka |
| 2010/0069948 A1 | 3/2010 | Veznedaroglu et al. |
| 2010/0174309 A1 | 7/2010 | Fulkerson |
| 2010/0217187 A1 | 8/2010 | Fulkerson |
| 2010/0256600 A1 | 10/2010 | Ferrera |
| 2010/0268204 A1 | 10/2010 | Tieu et al. |
| 2010/0318097 A1 | 12/2010 | Ferrera |
| 2011/0022149 A1 | 1/2011 | Cox |
| 2011/0040319 A1 | 2/2011 | Fulton, III |
| 2011/0046658 A1 | 2/2011 | Cormor et al. |
| 2011/0054519 A1 | 3/2011 | Neuss |

(56) References Cited

U.S. PATENT DOCUMENTS

| | | |
|---|---|---|
| 2011/0082491 A1 | 4/2011 | Sepetka |
| 2011/0152993 A1 | 6/2011 | Marchand et al. |
| 2011/0160763 A1 | 6/2011 | Ferrera et al. |
| 2011/0190797 A1 | 8/2011 | Fulkerson |
| 2011/0202085 A1 | 8/2011 | Loganathan et al. |
| 2011/0264132 A1 | 10/2011 | Strauss |
| 2011/0319926 A1 | 12/2011 | Becking et al. |
| 2011/0319978 A1 | 12/2011 | Schaffer |
| 2012/0016406 A1 | 1/2012 | Ferrera |
| 2012/0041460 A1 | 2/2012 | Ferrera |
| 2012/0041475 A1 | 2/2012 | Ferrera |
| 2012/0071911 A1 | 3/2012 | Sadasivan |
| 2012/0150147 A1 | 6/2012 | Leynov |
| 2012/0165919 A1 | 6/2012 | Cox |
| 2012/0172973 A1 | 7/2012 | Deckard et al. |
| 2012/0271337 A1 | 10/2012 | Figulla et al. |
| 2012/0283768 A1 | 11/2012 | Cox et al. |
| 2012/0330341 A1 | 12/2012 | Becking et al. |
| 2012/0330347 A1 | 12/2012 | Becking |
| 2013/0035628 A1 | 2/2013 | Garrison et al. |
| 2013/0035712 A1 | 2/2013 | Theobald et al. |
| 2013/0066357 A1 | 3/2013 | Aboytes et al. |
| 2013/0066360 A1 | 3/2013 | Becking |
| 2013/0066413 A1 | 3/2013 | Jin |
| 2013/0090682 A1 | 4/2013 | Bachman et al. |
| 2013/0123830 A1 | 5/2013 | Becking |
| 2013/0165967 A1 | 6/2013 | Amin |
| 2013/0190800 A1 | 7/2013 | Murphy |
| 2013/0197622 A1 | 8/2013 | Mitra et al. |
| 2013/0245667 A1 | 9/2013 | Marchand |
| 2013/0274862 A1 | 10/2013 | Cox |
| 2013/0274866 A1 | 10/2013 | Cox |
| 2013/0274868 A1 | 10/2013 | Cox et al. |
| 2014/0005714 A1 | 1/2014 | Quicket et al. |
| 2014/0012307 A1 | 1/2014 | Franano et al. |
| 2014/0012363 A1 | 1/2014 | Franano et al. |
| 2014/0052233 A1 | 2/2014 | Cox |
| 2014/0163609 A1 | 6/2014 | Solem |
| 2014/0172001 A1 | 6/2014 | Becking et al. |
| 2014/0200607 A1 | 7/2014 | Sepetka et al. |
| 2014/0257360 A1 | 9/2014 | Keillor |
| 2014/0257374 A1 | 9/2014 | Heisel et al. |
| 2014/0343602 A1 | 11/2014 | Cox et al. |
| 2014/0358178 A1 | 12/2014 | Hewitt et al. |
| 2015/0105817 A1 | 4/2015 | Marchand |
| 2015/0133990 A1 | 5/2015 | Davidson |
| 2015/0150563 A1 | 6/2015 | Marchand |
| 2015/0250628 A1 | 10/2015 | Monstadt |
| 2015/0272589 A1 | 10/2015 | Lorenzo |
| 2015/0313605 A1 | 11/2015 | Griffin |
| 2015/0351770 A1 | 12/2015 | Fulton, III |
| 2015/0351775 A1 | 12/2015 | Fulton, III |
| 2016/0106437 A1 | 4/2016 | Vanderburg |
| 2016/0113662 A1 | 4/2016 | Kobayashi et al. |
| 2016/0120551 A1 | 5/2016 | Conner |
| 2016/0174991 A1 | 6/2016 | Chin |
| 2016/0206321 A1 | 7/2016 | Connor |
| 2016/0213380 A1 | 7/2016 | O'Brien |
| 2016/0249934 A1 | 9/2016 | Hewitt et al. |
| 2016/0249935 A1* | 9/2016 | Hewitt ............. A61B 17/12177 606/200 |
| 2016/0345979 A1 | 12/2016 | Adams et al. |
| 2017/0128077 A1 | 5/2017 | Hewitt et al. |
| 2017/0156733 A1 | 6/2017 | Becking |
| 2017/0156734 A1 | 6/2017 | Griffin |
| 2017/0172581 A1 | 6/2017 | Bose |
| 2018/0125500 A1 | 5/2018 | Connor |
| 2018/0140305 A1 | 5/2018 | Connor |
| 2018/0193024 A1 | 7/2018 | Walzman |
| 2018/0193027 A1* | 7/2018 | Wang ............. A61B 17/12122 |
| 2018/0193043 A1 | 7/2018 | Marchand et al. |
| 2018/0206848 A1 | 7/2018 | Walzman |
| 2018/0206851 A1 | 7/2018 | Walzman |
| 2018/0214158 A1 | 8/2018 | Walzman |
| 2018/0333248 A1 | 11/2018 | Davidson |
| 2019/0008522 A1 | 1/2019 | Lorenzo |
| 2019/0053810 A1 | 2/2019 | Griffin |
| 2019/0059909 A1 | 2/2019 | Griffin |
| 2019/0110796 A1 | 4/2019 | Jayaraman |
| 2019/0183519 A1 | 6/2019 | Imai et al. |
| 2019/0209146 A1 | 7/2019 | Hebert |
| 2019/0209178 A1 | 7/2019 | Richter |
| 2019/0216467 A1 | 7/2019 | Goyal |
| 2019/0223876 A1 | 7/2019 | Badruddin |
| 2019/0223881 A1 | 7/2019 | Hewitt |
| 2019/0231328 A1 | 8/2019 | Hebert |
| 2019/0262002 A1 | 8/2019 | Benjamin |
| 2019/0269414 A1 | 9/2019 | Griffin |
| 2019/0274691 A1 | 9/2019 | Sepetka |
| 2019/0336132 A1 | 11/2019 | Warner |
| 2019/0343533 A1 | 11/2019 | Costalat |
| 2019/0357914 A1 | 11/2019 | Gorochow |
| 2019/0365472 A1 | 12/2019 | Connor |
| 2019/0374228 A1 | 12/2019 | Wallace |
| 2019/0380718 A1 | 12/2019 | Morsi |
| 2019/0388108 A1 | 12/2019 | Ferrera |
| 2020/0029973 A1 | 1/2020 | Walzman |
| 2020/0038032 A1 | 2/2020 | Rhee |
| 2020/0038035 A1 | 2/2020 | Griffin |
| 2020/0054344 A1 | 2/2020 | Connor |
| 2020/0060702 A1 | 2/2020 | Davidson |
| 2020/0069313 A1 | 3/2020 | Xu |
| 2020/0093499 A1 | 3/2020 | Lorenzo |
| 2020/0100795 A1 | 4/2020 | Connor |
| 2020/0113576 A1 | 4/2020 | Gorochow |
| 2020/0138422 A1 | 5/2020 | Hebert |
| 2020/0155333 A1 | 5/2020 | Franano |
| 2020/0163784 A1 | 5/2020 | Franano |
| 2020/0187952 A1 | 6/2020 | Walsh |
| 2020/0187978 A1 | 6/2020 | Walzman |
| 2020/0253766 A1 | 8/2020 | Walzman |
| 2020/0268365 A1 | 8/2020 | Hebert |
| 2020/0281603 A1 | 9/2020 | Marchand |
| 2020/0289124 A1 | 9/2020 | Rangwala |
| 2020/0289125 A1 | 9/2020 | Dholakia |
| 2020/0289126 A1 | 9/2020 | Hewitt |
| 2020/0305886 A1 | 10/2020 | Soto Del |
| 2020/0323534 A1 | 10/2020 | Shimizu |
| 2020/0337710 A1 | 10/2020 | Lorenzo |
| 2020/0340154 A1 | 10/2020 | Koppe |
| 2020/0345376 A1 | 11/2020 | Fulton, III |
| 2020/0367894 A1 | 11/2020 | Pereira |
| 2020/0367896 A1 | 11/2020 | Zaidat |
| 2020/0367897 A1 | 11/2020 | Wolfe |
| 2020/0367904 A1 | 11/2020 | Becking |
| 2020/0375606 A1 | 12/2020 | Lorenzo |
| 2020/0375607 A1 | 12/2020 | Soto Del Valle |
| 2020/0390455 A1 | 12/2020 | Nguyen et al. |
| 2020/0397447 A1 | 12/2020 | Lorenzo |
| 2020/0405347 A1 | 12/2020 | Walzman |
| 2021/0007755 A1 | 1/2021 | Lorenzo |
| 2021/0022765 A1 | 1/2021 | Walzman |
| 2021/0045750 A1 | 2/2021 | Wolfe |
| 2021/0068842 A1 | 3/2021 | Griffin |
| 2021/0077116 A1 | 3/2021 | Ferrera |
| 2021/0106337 A1 | 4/2021 | Hewitt |
| 2021/0128160 A1 | 5/2021 | Li |
| 2021/0128161 A1 | 5/2021 | Nageswaran |
| 2021/0128162 A1 | 5/2021 | Rhee |
| 2021/0128165 A1 | 5/2021 | Pulugurtha |
| 2021/0128166 A1 | 5/2021 | Kealey |
| 2021/0128167 A1 | 5/2021 | Patel |
| 2021/0128168 A1 | 5/2021 | Nguyen |
| 2021/0128169 A1 | 5/2021 | Li |
| 2021/0129275 A1 | 5/2021 | Nguyen |
| 2021/0137530 A1 | 5/2021 | Greene, Jr. et al. |
| 2021/0145449 A1 | 5/2021 | Gorochow |
| 2021/0153872 A1 | 5/2021 | Nguyen et al. |
| 2021/0169496 A1 | 6/2021 | Badruddin et al. |
| 2021/0169499 A1 | 6/2021 | Merritt et al. |
| 2021/0186518 A1 | 6/2021 | Gorochow et al. |
| 2021/0196284 A1 | 7/2021 | Gorochow et al. |
| 2021/0204955 A1 | 7/2021 | Wallace et al. |
| 2021/0219982 A1 | 7/2021 | Badruddin et al. |

(56) References Cited

U.S. PATENT DOCUMENTS

| | | |
|---|---|---|
| 2021/0251635 A1 | 8/2021 | Del Valle et al. |
| 2021/0259719 A1 | 8/2021 | Griffin |
| 2021/0275184 A1 | 9/2021 | Hewitt et al. |
| 2021/0275188 A1 | 9/2021 | Plaza et al. |
| 2021/0282784 A1 | 9/2021 | Sepetka et al. |
| 2021/0282786 A1 | 9/2021 | Zaidat et al. |
| 2021/0330331 A1 | 10/2021 | Lorenzo |
| 2021/0346032 A1 | 11/2021 | Patterson et al. |
| 2021/0361290 A1 | 11/2021 | Badruddin et al. |
| 2021/0378646 A1 | 12/2021 | Amplatz et al. |
| 2021/0401439 A1 | 12/2021 | Lorenzo et al. |
| 2022/0022884 A1 | 1/2022 | Wolfe et al. |
| 2022/0022886 A1 | 1/2022 | Becking et al. |
| 2022/0054141 A1 | 2/2022 | Zaidat et al. |
| 2022/0054286 A1 | 2/2022 | Goyal |

FOREIGN PATENT DOCUMENTS

| | | |
|---|---|---|
| CN | 103099652 | 5/2013 |
| CN | 103142261 | 6/2013 |
| CN | 104168843 | 11/2014 |
| CN | 104958087 | 10/2015 |
| CN | 204931771 | 1/2016 |
| CN | 204971420 | 1/2016 |
| DE | 102008028308 | 4/2009 |
| DE | 102008015781 | 9/2011 |
| DE | 102011102955 | 12/2012 |
| DE | 102009058132 | 7/2014 |
| DE | 202008018523 | 4/2015 |
| DE | 102013106031 | 7/2015 |
| DE | 102012107175 | 8/2015 |
| DE | 102012102844 | 3/2020 |
| DE | 102019121546 | 2/2021 |
| DE | 102019121554 | 2/2021 |
| EP | 0836450 | 4/1998 |
| EP | 0902704 | 3/1999 |
| EP | 1003422 | 5/2000 |
| EP | 1295563 | 3/2003 |
| EP | 1441649 | 8/2004 |
| EP | 1483009 | 12/2004 |
| EP | 1494619 | 1/2005 |
| EP | 1527753 | 5/2005 |
| EP | 1569565 | 9/2005 |
| EP | 1574169 | 9/2005 |
| EP | 1054635 | 11/2005 |
| EP | 1610666 | 1/2006 |
| EP | 1633275 | 3/2006 |
| EP | 1651117 | 5/2006 |
| EP | 1659988 | 5/2006 |
| EP | 1725185 | 11/2006 |
| EP | 1804719 | 7/2007 |
| EP | 1862122 | 12/2007 |
| EP | 1923005 | 5/2008 |
| EP | 1923019 | 5/2008 |
| EP | 2063791 | 6/2009 |
| EP | 2134263 | 12/2009 |
| EP | 2157937 | 3/2010 |
| EP | 2207500 | 7/2010 |
| EP | 2244666 | 11/2010 |
| EP | 2265193 | 12/2010 |
| EP | 2266465 | 12/2010 |
| EP | 2279023 | 2/2011 |
| EP | 2324775 | 5/2011 |
| EP | 2349024 | 8/2011 |
| EP | 2367482 | 9/2011 |
| EP | 2387951 | 11/2011 |
| EP | 2399524 | 12/2011 |
| EP | 2460476 | 6/2012 |
| EP | 2460478 | 6/2012 |
| EP | 2468349 | 6/2012 |
| EP | 2496299 | 9/2012 |
| EP | 2506808 | 10/2012 |
| EP | 2543345 | 1/2013 |
| EP | 2567663 | 3/2013 |
| EP | 2596754 | 5/2013 |
| EP | 2613709 | 7/2013 |
| EP | 2617386 | 7/2013 |
| EP | 2618709 | 7/2013 |
| EP | 2647343 | 10/2013 |
| EP | 2677944 | 1/2014 |
| EP | 2744412 | 6/2014 |
| EP | 2848211 | 3/2015 |
| EP | 2854704 | 4/2015 |
| EP | 2887887 | 7/2015 |
| EP | 2923674 | 9/2015 |
| EP | 2926744 | 10/2015 |
| EP | 2943152 | 11/2015 |
| EP | 2964105 | 1/2016 |
| EP | 3068337 | 9/2016 |
| EP | 3082619 | 10/2016 |
| EP | 3131515 | 2/2017 |
| EP | 3136986 | 3/2017 |
| EP | 3148481 | 4/2017 |
| EP | 3151904 | 4/2017 |
| EP | 3171793 | 5/2017 |
| EP | 3187117 | 7/2017 |
| EP | 3247285 | 11/2017 |
| EP | 3261703 | 1/2018 |
| EP | 1998686 | 2/2018 |
| EP | 2460477 | 4/2018 |
| EP | 3345553 | 7/2018 |
| EP | 2806825 | 8/2018 |
| EP | 2753246 | 11/2018 |
| EP | 3413808 | 12/2018 |
| EP | 3429479 | 1/2019 |
| EP | 3456271 | 3/2019 |
| EP | 3456272 | 3/2019 |
| EP | 3501429 | 6/2019 |
| EP | 2254505 | 7/2019 |
| EP | 3510945 | 7/2019 |
| EP | 3512459 | 7/2019 |
| EP | 3517055 | 7/2019 |
| EP | 2194885 | 11/2019 |
| EP | 3572010 | 11/2019 |
| EP | 3173037 | 12/2019 |
| EP | 3574851 | 12/2019 |
| EP | 3585275 | 1/2020 |
| EP | 3600068 | 2/2020 |
| EP | 3622901 | 3/2020 |
| EP | 3628242 | 4/2020 |
| EP | 3636173 | 4/2020 |
| EP | 2405820 | 6/2020 |
| EP | 3669800 | 6/2020 |
| EP | 3677192 | 7/2020 |
| EP | 3714812 | 9/2020 |
| EP | 3153114 | 11/2020 |
| EP | 3740138 | 11/2020 |
| EP | 3755276 | 12/2020 |
| EP | 3501428 | 4/2021 |
| EP | 3568088 | 4/2021 |
| EP | 3808284 | 4/2021 |
| EP | 3821825 | 5/2021 |
| EP | 3838186 | 6/2021 |
| EP | 3865079 | 8/2021 |
| EP | 3908208 | 11/2021 |
| EP | 3908209 | 11/2021 |
| EP | 3908354 | 11/2021 |
| FR | 3061647 | 6/2020 |
| IL | 248515 | 7/2019 |
| JP | H02150481 | 6/1990 |
| JP | H0447415 | 4/1992 |
| JP | H0850701 I | 7/1996 |
| JP | 2003-175113 | 6/2003 |
| JP | 2005028863 | 2/2005 |
| JP | 2005537092 | 12/2005 |
| JP | 2006509578 | 3/2006 |
| JP | 2010500187 | 1/2010 |
| JP | 2012-501793 | 1/2012 |
| JP | 2012030497 | 2/2012 |
| JP | 2013-027592 | 2/2013 |
| JP | 2013537069 | 9/2013 |
| RU | 2018131107 | 10/2018 |
| RU | 2019120682 | 9/2019 |
| RU | 2704539 | 10/2019 |

(56) References Cited

FOREIGN PATENT DOCUMENTS

| | | |
|---|---|---|
| RU | 2018145502 | 6/2020 |
| RU | 2018145543 | 6/2020 |
| RU | 2019110988 | 10/2020 |
| RU | 2019115837 | 11/2020 |
| RU | 2019116175 | 11/2020 |
| RU | 2019127900 | 3/2021 |
| RU | 2019129351 | 3/2021 |
| RU | 2019129526 | 3/2021 |
| WO | 2006/034149 | 3/2006 |
| WO | 2006/052322 | 5/2006 |
| WO | 2007/076480 | 7/2007 |
| WO | 2007/079402 | 7/2007 |
| WO | 2008/036156 | 3/2008 |
| WO | 2008/151204 | 12/2008 |
| WO | 2009/135166 | 11/2009 |
| WO | 2010/030991 | 3/2010 |
| WO | 2010/134914 | 11/2010 |
| WO | 2011/057002 | 5/2011 |
| WO | 2012/032030 | 3/2012 |
| WO | 2012/034135 | 3/2012 |
| WO | 2012/099704 | 7/2012 |
| WO | 2012/099909 | 7/2012 |
| WO | 2012/099910 | 7/2012 |
| WO | 2012/135037 | 10/2012 |
| WO | 2012/163880 | 12/2012 |
| WO | 2013/016618 | 1/2013 |
| WO | 2013005195 | 1/2013 |
| WO | 2013/028579 | 2/2013 |
| WO | 2013/103888 | 7/2013 |
| WO | 2013/109309 | 7/2013 |
| WO | 2012/113554 | 8/2013 |
| WO | 2013/152327 | 10/2013 |
| WO | 2013/184595 | 12/2013 |
| WO | 2014/029835 | 2/2014 |
| WO | 2015/095538 | 6/2015 |
| WO | 2015/160721 | 10/2015 |
| WO | 2015/166013 | 11/2015 |
| WO | 2015/184075 | 12/2015 |
| WO | 2015/187196 | 12/2015 |
| WO | 2016/107357 | 7/2016 |
| WO | 2016/118420 | 7/2016 |
| WO | 2016/137997 | 9/2016 |
| WO | 2017/106567 | 6/2017 |
| WO | 2017/139702 | 8/2017 |
| WO | 2017/156275 | 9/2017 |
| WO | 2017/161283 | 9/2017 |
| WO | 2018/051187 | 3/2018 |
| WO | 2018/130624 | 7/2018 |
| WO | 2018/156833 | 8/2018 |
| WO | 2018/175221 | 9/2018 |
| WO | 2019/143755 | 7/2019 |
| WO | 2019/165360 | 8/2019 |
| WO | 2020/139544 | 7/2020 |
| WO | 2020/150023 | 7/2020 |
| WO | 2020/190620 | 9/2020 |
| WO | 2020/190630 | 9/2020 |
| WO | 2020/190639 | 9/2020 |
| WO | 2020/243039 | 12/2020 |
| WO | 2021/028160 | 2/2021 |
| WO | 2021/028161 | 2/2021 |
| WO | 2021/051110 | 3/2021 |
| WO | 2021/087610 | 5/2021 |
| WO | 2021/092620 | 5/2021 |
| WO | 2021/183793 | 9/2021 |

OTHER PUBLICATIONS

JP Office Action in Japanese Application No. 2018-529554, dated Jul. 12, 2021, 6 pages (with English translation).
JP Office Action in Japanese Application No. 2018-529554, dated Sep. 15, 2020, 6 pages (with English translation).
JP Office Action in Japanese Application No. 2019-145966, dated Sep. 1, 2020, 6pages (with English translation).
PCT International Preliminary Report on Patentability in International Application No. PCT/EP2016/080152, dated Jun. 12, 2018, 10 pages.
PCT International Preliminary Report on Patentability in International Application No. PCT/EP2017/055765, dated Sep. 11, 2018, 9 pages.
PCT International Written Opinion in International Application No. PCT/EP2021/054103, dated Aug. 26, 2021, 4 pages.
Bosworth et al., "Gamma irradiation of electrospun poly(£-caprolactone) fibers affects material properties but not cell response," Journal of Polymer Science Part B: Polymer Physics, Apr. 2012, pp. 870-876.
CA Office Action in Canadian Appl. No. 2,946,078, dated May 26, 2021, 4 pages.
CN Office Action in Chinese Appln. No. 201580035663.X, dated Aug. 1, 2018, 27 pages (with English Translation).
CN Office Action in Chinese Appln. No. 201780024233.7, dated Jul. 9, 2020, 20 pages (with English Translation).
CN Office Action in Chinese Appln. No. 201780024233.7, dated Oct. 22, 2020, 17 pages (with English Translation).
EP Extended Search Report in European Appln. No. 19159876.2, dated Jun. 14, 2019, 9 pages.
EP Extended Search Report in European Appln. No. 20201759.6, dated Nov. 12, 2020, 12 pages.
EP Office Action in European Appln No. 16808631.2, dated Aug. 16, 2019, 8 pages.
Izadi et al., "Teflon hierarchical nanopillars with dry and wet adhesive properties," Journal of Polymer Science Part B: Polymer Physics, Apr. 2012, pp. 846-851.
Ohta et al., "Size control of phase-separated liquid crystal droplets in a polymer matrix based on the phase diagram," Journal of Polymer Science Part B: Polymer Physics, Apr. 2012, pp. 863-869.
Popov et al., "Interacting nanoparticles with functional surface groups," Journal of Polymer Science Part B: Polymer Physics, Mar. 2012, pp. 852-862.
EP Extended European Search Report in European Appln. No. 17710255.5, dated Nov. 12. 2020. 12 pages.
JP Office Action in Japanese Appln. No. 2018-529554, dated Nov. 30, 2020, 11 pages (with English translation).
JP Office Action in Japanese Appln. No. 2018-548075, dated Mar. 25, 2021, 8 pages (with English translation).
CN Office Action in Chinese Appln. No. 201780024233.7, dated Apr. 22, 2021, 6 pages (with English translation).
Altes et al., "Creation of Saccular Aneurysms in the Rabbit: A Model Suitable for Testing Endovascular Devices," AJR Arn J Roentgenol, 2000, 174(2):349-354.
Blackshear et al., "Appendage obliteration to reduce stroke in c<irdiac surgical patients v. th atrial fibrillation," Ann. Thorac. Surg., Feb. 1996, 61(2):755-9.
Gottlieb et al., "Anticoagulation in atrial fibrillation. Does efficacy in clinical trials translate into effectiveness in oractice?" Arch. Intern. Med., S<>ntember 1994, 154(17):1945-53.
International Preliminary Report on Patentability in International Application No. PCT/EP2015/059429, dated Jul. 13, 2016, 11 pages.
International Search Report and Written Opinion in International Application No. PCTIEP2016/080152, dated Jun. 16, 2017, 8 pages.
International Search Report and Written Opinion in International Appln. No. PCT/EP2018/072576, dated Nov. 21, 2018, 20 pages.
International Search Report and Written Opinion in International Appln. PCT/EP2015/059429, dated Jul. 6, 2015, 5 pages.
PCT International Search Report in International Appln. PCT/EP2017 /055765, dated Apr. 18, 2017, 5 pages.
JP Office Action in Japanese Appln. No. 2017-508761, d<lted Nov. 27, 2018, 4 pages (English tnmslation).
JP Office Action in Japanese Appln. No. 2017-508761, dated Mar. 19, 2019, 3 pages (English translation).
PCT Form ISA/206—Invitation To Pay Additional Fees in International Appln. PCT/EP2016/080152, dated Feb. 24, 2017, 9 pages.
PCT International Preliminary Report on Patentability in International Appln. No. PCT/EP2019/072576, dated Feb. 25, 2020, 13 pages.

(56) References Cited

OTHER PUBLICATIONS

Schaffer, "Biocompatible Wire," Advanced Materials & Processes, Oct. 2002, pp. 51-54.
Third Office Action issued by the Chinese Patent Office in Application No. 201880068541.4 dated Sep. 20, 2023. (English translation included).

* cited by examiner

OCCLUSION DEVICE

RELATED APPLICATIONS

This application is a continuation of U.S. patent application Ser. No. 16/640,142 filed on Feb. 19, 2020, which is a National Stage Entry pursuant to 35 U.S.C. § 371 of International Application No. PCT/EP2018/072576 filed Aug. 21, 2018, which claims priority to U.S. Provisional Application No. 62/547,966 filed Aug. 21, 2017. All documents and references cited herein and in the above referenced applications, are hereby incorporated by reference.

FIELD OF THE INVENTION

The occlusion device disclosed herein relates generally to the field of occlusion devices and/or occlusion device systems and/or implantable occlusion devices and the use of the same for the occlusion of vessels and/or the treatment and/or amelioration of aneurysms and/or for peripheral vascular embolization (a process well known in the art and known to involve the shutdown of blood flow distal to a specified vascular point), for example, in the treatment and/or amelioration of peripheral arterial or venous pathologies and/or any related pathologies requiring vessel occlusion for the treatment thereof.

BACKGROUND OF THE DISCLOSURE

There is a significant demand for the development of improved occlusion devices and/or systems for the treatment and/or amelioration of aneurysms. This observation is supported by the abundance and wide-range of current occlusion devices and/or systems currently in the aneurysm peripheral vascular embolization treatment field. However, there still remains an unmet need for providing aneurysm treatment and/or amelioration, particularly for neurovascular aneurysms, via occlusion devices comprised of a deployable material designed to achieve greater flow disruption and compartmentalization to introduce stasis and/or designed in such a manner so as to occlude larger and/or more irregularly shaped aneurysms.

It is well known that an aneurysm forms when a dilated portion of an artery is stretched thin from the pressure of the blood. The weakened part of the artery forms a bulge, or a ballooning area, that risks leak and/or rupture. When a neurovascular aneurysm ruptures, it causes bleeding into the compartment surrounding the brain, the subarachnoid space, causing a subarachnoid hemorrhage. Subarachnoid hemorrhage from a ruptured neurovascular aneurysm can lead to a hemorrhagic stroke, brain damage, and death. Approximately 25 percent of all patients with a neurovascular aneurysm suffer a subarachnoid hemorrhage. Neurovascular aneurysms occur in two to five percent of the population and more commonly in women than men. It is estimated that as many as 18 million people currently living in the United States will develop a neurovascular aneurysm during their lifetime. Annually, the incidence of subarachnoid hemorrhage in the United States exceeds 30,000 people. Ten to fifteen percent of these patients die before reaching the hospital and over 50 percent die within the first thirty days after rupture. Of those who survive, about half suffer some permanent neurological deficit.

Smoking, hypertension, traumatic head injury, alcohol abuse, use of hormonal contraception, family history of brain aneurysms, and other inherited disorders such as Ehlers-Danlos syndrome (EDS), polycystic kidney disease, and Marfan syndrome possibly contribute to neurovascular aneurysms.

Most unruptured aneurysms are asymptomatic. Some people with unruptured aneurysms experience some or all of the following symptoms: peripheral vision deficits, thinking or processing problems, speech complications, perceptual problems, sudden changes in behavior, loss of balance and coordination, decreased concentration, short term memory difficulty, and fatigue. Symptoms of a ruptured neurovascular aneurysm include nausea and vomiting, stiff neck or neck pain, blurred or double vision, pain above and behind the eye, dilated pupils, sensitivity to light, and loss of sensation. Sometimes patients describing "the worst headache of my life" are experiencing one of the symptoms of a ruptured neurovascular aneurysm.

Most aneurysms remain undetected until a rupture occurs. Aneurysms, however, may be discovered during routine medical exams or diagnostic procedures for other health problems. Diagnosis of a ruptured cerebral aneurysm is commonly made by finding signs of subarachnoid hemorrhage on a CT scan (Computerized Tomography). If the CT scan is negative but a ruptured aneurysm is still suspected, a lumbar puncture is performed to detect blood in the cerebrospinal fluid (CSF) that surrounds the brain and spinal cord.

To determine the exact location, size, and shape of an aneurysm, neuroradiologists use either cerebral angiography or tomographic angiography. Cerebral angiography, the traditional method, involves introducing a catheter into an artery (usually in the leg) and steering it through the blood vessels of the body to the artery involved by the aneurysm. A special dye, called a contrast agent, is injected into the patient's artery and its distribution is shown on X-ray projections. This method may not detect some aneurysms due to overlapping structures or spasm.

Computed Tomographic Angiography (CTA) is an alternative to the traditional method and can be performed without the need for arterial catheterization. This test combines a regular CT scan with a contrast dye injected into a vein. Once the dye is injected into a vein, it travels to the brain arteries, and images are created using a CT scan. These images show exactly how blood flows into the brain arteries. New diagnostic modalities promise to supplement both classical and conventional diagnostic studies with less-invasive imaging and possibly provide more accurate 3-dimensional anatomic information relative to aneurismal pathology. Better imaging, combined with the development of improved minimally invasive treatments, will enable physicians to increasingly detect, and treat, more silent aneurysms before problems arise.

Several methods of treating aneurysms have been attempted, with varying degrees of success. For example, open craniotomy is a procedure by which an aneurysm is located, and treated, extravascularly. This type of procedure has significant disadvantages. For example, the patient undergoes a great deal of trauma in the area of the aneurysm by virtue of the fact that the surgeon must sever various tissues in order to reach the aneurysm. In treating cerebral aneurysms extravascularly, for instance, the surgeon must typically remove a portion of the patient's skull, and must also traumatize brain tissue in order to reach the aneurysm. As such, there is a potential for the development of epilepsy in the patients due to the surgery.

Other techniques used in treating aneurysms are performed endovascularly. Such techniques typically involve attempting to form a mass within the sac of the aneurysm.

Typically, a microcatheter is used to access the aneurysm. The distal tip of the microcatheter is placed within the sac of the aneurysm, and the microcatheter is used to inject embolic material into the sac of the aneurysm. The embolic material includes, for example, detachable coils or an embolic agent, such as a liquid polymer. The injection of these types of embolic materials suffers from disadvantages, most of which are associated with migration of the embolic material out of the aneurysm into the parent artery. This can cause permanent and irreversible occlusion of the parent artery.

For example, when detachable coils are used to occlude an aneurysm which does not have a well-defined neck region, the detachable coils can migrate out of the sac of the aneurysm and into the parent artery. Further, it is at times difficult to gauge exactly how full the sac of the aneurysm is when detachable coils are deployed. Therefore, there is a risk of overfilling the aneurysm in which case the detachable coils also spill out into the parent artery.

Another disadvantage of detachable coils involves coil compaction over time. After filling the aneurysm, there remains space between the coils. Continued hemodynamic forces from the circulation act to compact the coil mass resulting in a cavity in the aneurysm neck. Thus, the aneurysm can recanalize.

Embolic agent migration is also a problem. For instance, where a liquid polymer is injected into the sac of the aneurysm, it can migrate out of the sac of the aneurysm due to the hemodynamics of the system. This can also lead to irreversible occlusion of the parent vessel.

Techniques have been attempted in order to deal with the disadvantages associated with embolic material migration to the parent vessel. Such techniques are, without limitation, temporary flow arrest and parent vessel occlusion, and typically involve temporarily occluding the parent vessel proximal of the aneurysm, so that no blood flow occurs through the parent vessel, until a thrombotic mass has formed in the sac of the aneurysm. In theory, this helps reduce the tendency of the embolic material to migrate out of the aneurysm sac. However, it has been found that a thrombotic mass can dissolve through normal lysis of blood. Also, in certain cases, it is highly undesirable from a patient's risk/benefit perspective to occlude the parent vessel, even temporarily. Therefore, this technique is, at times, not available as a treatment option. In addition, it is now known that even occluding the parent vessel may not prevent all embolic material migration into the parent vessel.

Another endovascular technique for treating aneurysms involves inserting a detachable balloon into the sac of the aneurysm using a microcatheter. The detachable balloon is then inflated using saline and/or contrast fluid. The balloon is then detached from the microcatheter and left within the sac of the aneurysm in an attempt to fill the sac of the aneurysm. However, detachable balloons also suffer disadvantages and as such this practice has all but been superseded by the current practice of deployment of coils or other types of occlusion devices. For example, detachable balloons, when inflated, typically will not conform to the interior configuration of the aneurysm sac. Instead, the detachable balloon requires the aneurysm sac to conform to the exterior surface of the detachable balloon. Thus, there is an increased risk that the detachable balloon will rupture the sac of the aneurysm. Further, detachable balloons can rupture and migrate out of the aneurysm.

Another endovascular technique for treating aneurysms involves occlusion devices having two expandable lobes and a waist, or an expandable body portion, a neck portion, and a base portion.

Still another endovascular technique for treating aneurysms involves occlusion devices for intrasaccular implantation having a body portion designed to fill and/or expand radially into the space within the sac of the aneurysm.

Still other endovascular techniques are disclosed in the co-owned pending applications, U.S. Ser. No. 14/699,188 and U.S. Ser. No. 15/372,128, incorporated herein in their entirety by reference.

Many current occlusion devices are not designed for treatment of large aneurysms or for aneurysms of irregular shapes and sizes, including wide- and narrow-necked aneurysms, side-wall and bifurcation aneurysms, for example. Many current occlusion devices are constructed of braided or woven mesh designs and such designs, if reconfigured for a large and irregular shaped aneurysm, would typically utilize too much material. This would make it difficult to collapse down into a constrained, low profile, delivery configuration small enough to be delivered and deployed without excess friction on the walls of the delivery catheter or other delivery lumen. The sheer bulkiness of these devices would make them inconvenient or inappropriate for intra-cranial delivery.

Therefore, the occlusion device disclosed herein provides innovative improvements and several advantages in the field of vascular occlusion devices because the occlusion device disclosed herein provides aneurysm and/or body lumen treatment and/or amelioration, particularly for neurovascular aneurysms of large and irregular sizes, via the use of super compactable continuous mesh-based fully-retrievable deployable material. The occlusion device disclosed herein relates to a continuous configuration comprising disproportionate mesh bodies on opposing sides of a medial pinch point or marker. On one side of the pinch point or marker is a disc-shaped mesh body which caves inward like a cup. On the other opposing side of the pinch point or marker is a compressible mesh basket-shaped carriage defined on either axial end by a pinch point of the mesh or by a pinch point-encircled marker. This novel design achieves greater flow disruption and compartmentalization within the aneurysm or body lumen and results in increased stasis particularly so as to occlude larger and more irregularly shaped aneurysms.

All documents and references cited herein and in the referenced patent documents, are hereby incorporated herein by reference.

SUMMARY OF THE INVENTION

The present inventor has designed an intra-aneurysmal occlusion device for deploying into the aneurysm sac providing aneurysm treatment and/or amelioration through the creation of flow disruption and ultimate stasis. The occlusion device uniquely comprises a continuous mesh configuration having disproportionate mesh bodies on either side of a medial pinch point or marker providing a continuous 3-dimensional mesh network inside the aneurysm for flow disruption, thrombus establishment, and/or a framework for cell growth. Such an implantable occlusion device is also used for treatment of vessel occlusion and/or peripheral vascular embolization.

Disclosed herein is an occlusion device comprising: (a) continuous mesh structure comprising a medial pinch point; (b) a resilient mesh disc-shaped body extending distally and outward from the medial pinch point; and (c) a compressible mesh carriage extending distally from the medial pinch point on an opposing side of the resilient mesh body of (b), wherein the compressible mesh carriage comprises a pinch point on each end of the carriage, wherein one of the pinch points is the medial pinch point of (a); wherein the continuous mesh structure has a first delivery shape and a second expandable deployed shape, and wherein the length (x) of the resilient mesh body is greater than the length (y) of the compressible mesh carriage in free air and in the deployed shape.

In one embodiment, a marker encircles at least one pinch point of the continuous mesh structure. In a further embodiment, the marker is radiopaque. In further embodiments, a marker located at the distal (non-medial) end of the mesh carriage is a detachment junction to deploy the occlusion device and/or an attachment junction to retrieve the occlusion device. In still further embodiments, the marker comprises or the markers comprise a rigid member, and/or the marker is (or markers are) a solid ring(s).

In another embodiment, the continuous mesh structure expands to a deployed shape and fills the body lumen or aneurysm.

In one embodiment, the continuous mesh structure has an open mesh density for enhanced tissue integration and/or stabilization of the occlusion device.

In another embodiment, the resilient mesh body of the occlusion device is single-layer mesh.

In another embodiment, the resilient mesh body of the occlusion device is a dual or double layer mesh. In a further embodiment, the dual layer of mesh comprises a single layer of mesh folded circumferentially.

In another embodiment, at the mesh carriage of the continuous mesh structure comprises an inner coaxial mesh carriage or inner coaxial mesh carriages. In a further embodiment, the inner coaxial mesh carriage or carriages is dissimilar material to its outer mesh carriage. In a further embodiment, the inner coaxial mesh carriages are two (2) or three (3) inner coaxial mesh carriages. In another further embodiment, the inner coaxial mesh carriage or carriages is dissimilar mesh density to its outer mesh carriage.

In another embodiment, the continuous mesh structure is constructed from a super elastic material. In a further embodiment, the resilient mesh body is constructed from nitinol. In yet another embodiment, the resilient mesh body is constructed from DFT platinum core nitinol.

Also disclosed herein is a kit comprising the occlusion device disclosed herein and a delivery means for deploying the occlusion device.

Additionally disclosed herein are methods for manufacture and/or delivery and/or deployment of the occlusion device disclosed herein.

In other embodiments, the occlusion device in the preceding paragraphs may incorporate any of the preceding or subsequently disclosed embodiments.

The Summary of the Invention is not intended to define the claims nor is it intended to limit the scope of the invention in any manner.

Other features and advantages of the invention will be apparent from the following Drawings, Detailed Description, and the Claims.

DETAILED DESCRIPTION

Figure 1:
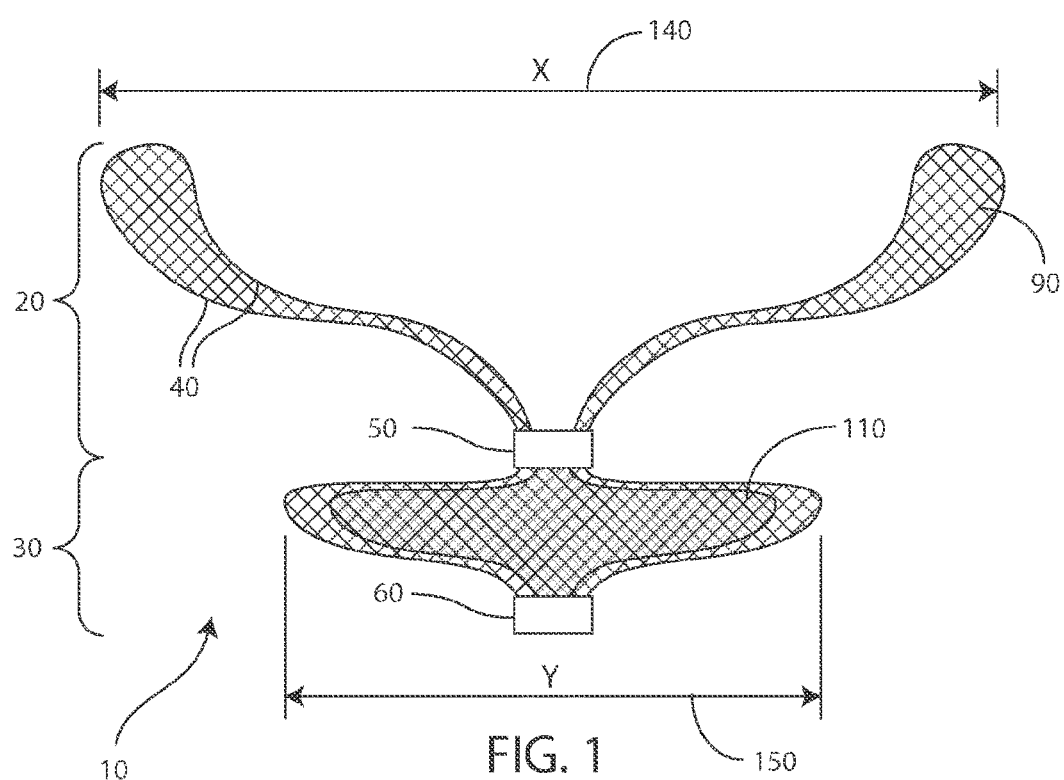
FIG. 1 illustrates a cross section of an embodiment of the occlusion device disclosed herein showing length (x) of the resilient mesh disc-shaped body is greater than the length (y) of the compressible mesh carriage in free air.

The present invention is illustrated in the drawings and description in which like elements are assigned the same reference numerals. However, while particular embodiments are illustrated in the drawings, there is no intention to limit the present invention to the specific embodiment or embodiments disclosed. Rather, the present invention is intended to cover all modifications, alternative constructions, and equivalents falling within the spirit and scope of the invention. As such, the drawings are intended to be illustrative and not restrictive.

Unless otherwise defined, all technical terms used herein have the same meaning as commonly understood by one of ordinary skill in the art to which this technology belongs.

Figure 2:
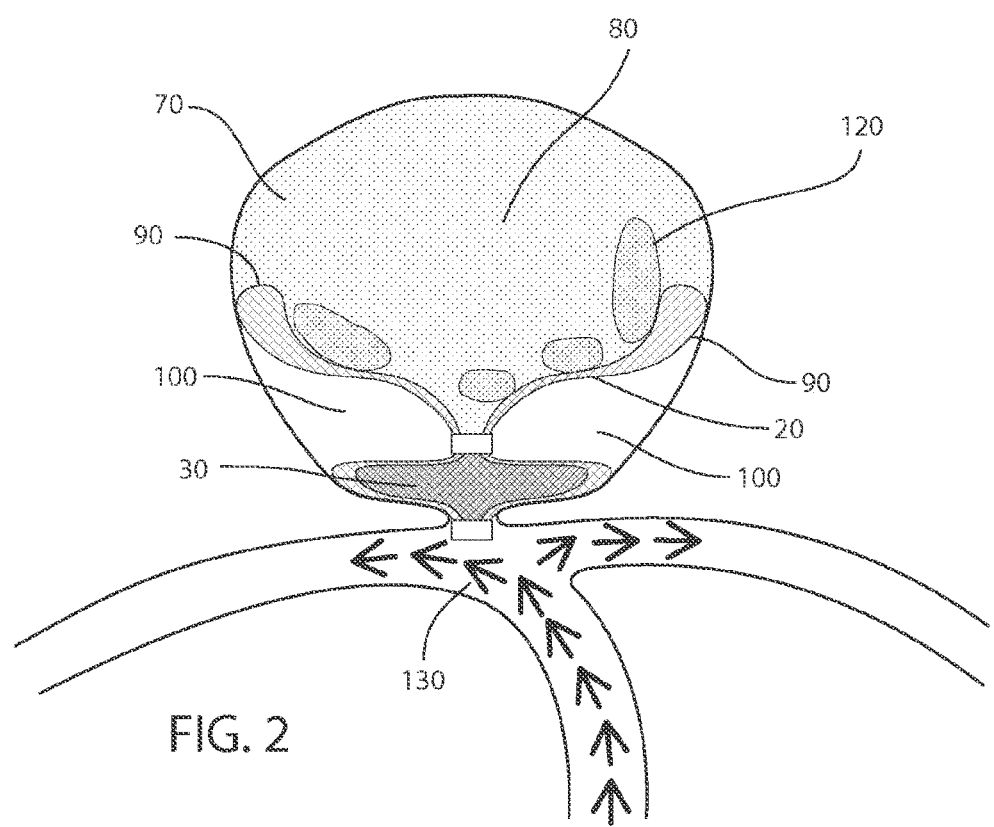
FIG. 2 illustrates an embodiment of the occlusion device disclosed herein deployed in an aneurysm showing the length (x) of the resilient mesh disc-shaped body is greater than the length (y) of the compressible mesh carriage in the deployed shape.

Exemplary embodiments of the occlusion device disclosed herein are depicted in FIGS. 1-2.

For the purposes of the occlusion device 10 disclosed herein, the terminology "corresponds to" means there is a functional and/or mechanical relationship between objects which correspond to each other. For example, an occlusion device delivery system corresponds to (or is compatible with) an occlusion device for deployment thereof.

For the purposes of the occlusion device 10 disclosed herein, the terminology "occlusion device" means and/or may be interchangeable with terminology such as, without limitation, "device" or "occlusion device system" or "occlusion system" or "system" or "occlusion device implant" or "implant" or "intrasaccular implant" or "intra-aneurysmal implant" and the like.

Occlusion device delivery systems are well known and readily available in the art. For example, such delivery technologies may be found, without limitation, in US Patent and Publication Numbers U.S. Pat. Nos. 4,991,602; 5,067,489; 6,833,003; 2006/0167494; and 2007/0288083; each of the teachings of which are incorporated herein. For the purposes of the occlusion device disclosed herein, any type of occlusion device delivery means and/or delivery system and/or delivery technology and/or delivery mechanism and/or detachment (and/or attachment) means and/or detachment system and/or detachment technology and/or detachment mechanism may be utilized and/or modified in such a manner as to make compatible (so as to correspond) with the occlusion device disclosed herein. Exemplary occlusion device delivery mechanisms and/or systems include, without limitation, guide wires, pusher wires, catheters, micro-catheters, and the like. Exemplary occlusion device detachment mechanisms include, without limitation, fluid pressure, electrolytic mechanisms, hydraulic mechanisms, interlocking mechanisms, and the like. In one embodiment, the occlusion device disclosed herein is used in a method of electrolytic detachment. Electrolytic detachment is well known in the art and can be found, for example, in U.S. Pat. Nos. 5,122,136; 5,423,829; 5,624,449; 5,891,128; 6,123,714; 6,589,230; and 6,620,152.

The occlusion device 10 disclosed herein relates to a continuous mesh configuration comprising disproportionate mesh structures on opposing sides of a medial pinch point or pinch point-encircled marker 50. On one side of the pinch point or marker is a disc-shaped mesh body 20 which caves inward like a cup. The disc-shaped expansion of the mesh body 20 is the result of the body having no other pinch point or pinch point-encircled marker than the medial pinch point or pinch point-encircled marker 50. Therefore, there is no pinch point or marker conforming the ends of the body into a sphere and rather the ends of the disc-shaped body 20 extend distally and outward allowing the protruding mesh 90 to appose the dome of the aneurysm 70, and effectively conform to the walls of the aneurysm 70 as the mesh disc-shaped body 20 caves inward in a cupped configuration. On the opposing side of the disc-shaped body 20 extending distally from the medial pinch point or pinch point-encircled marker 50 is a compressible mesh basket-shaped carriage 30 defined on either axial end by a pinch point of the mesh or by a pinch point-encircled marker 50, 60.

FIGS. 1-4 show a continuous mesh structure comprising a medial pinch point 50, a resilient mesh disc-shaped body 20 extending distally and outward from the medial pinch point 50 and a compressible mesh carriage 30 extending distally from the medial pinch point on an opposing side of the resilient mesh disc-shaped body 20. The compressible mesh carriage 30 comprises a pinch point on each end of the carriage, wherein one of the pinch points is the medial pinch point 50 of the entire continuous mesh structure. The device 10 disclosed herein has a continuous mesh structure which is capable of a first delivery shape and a second expandable deployed shape. FIG. 1 shows that, in one embodiment of the device 10 disclosed herein, the length (x) 140 of the resilient mesh body is greater than the length (y) 150 of the compressible mesh carriage 30 in free air and in the deployed shape. The continuous mesh structure of the device 10 disclosed herein and its uniquely disproportionate mesh substructures on either side of a medial pinch point 50 promotes more effective endothelialization around the device 10 as shown when the device is in the deployed shape in FIGS. 2 & 4. As such, the occlusion device 10 design is one continuous 3-dimensional mesh network which, when deployed in an aneurysm 70 or body lumen, provides flow disruption 130, thrombus 120 establishment, a framework for cell growth, and/or ultimate blood stasis 80.

For the purposes of the claimed invention, a "carriage" 30 is an axial segment of mesh between a pinch point of mesh or marker-encircled pinch point 50, 60 of mesh which causes the mesh to expand in a puffed yet compressed basket-shaped 110 manner. A "pinch point" is located at and defines the ends of an axial segment of mesh. Such segmented mesh carriages 30 and pinch points are configured to be within a continuous mesh structure or network. A "pinch point" is a constrained and gathered location on the mesh structure which functions to restrict movement of the adjacent carriage 30 at an isolated point and thereby stabilizes the carriage 30. In one embodiment of the continuous mesh structure of the device 10 disclosed herein, the pinch points stabilize the carriage 30 relative to the disc-shaped mesh body 20 extending distally therefrom a pinch point located at one axial end of the carriage 30 which is located medially 50 in relation to the entire continuous mesh structure. In one further embodiment, the continuous mesh structure comprises more than one mesh carriage 30. The number (n) of carriages 30 is as many as clinically and practically possible, and determined by a clinician in accordance with known diagnostic techniques in advance, for treating large and/or irregular-sized aneurysms 70, and for delivery through about a 150 centimeter (cm) catheter (or micro-catheter). The axial length (l) of each carriage 30 can vary depending on the number (n) of carriages 30 deemed appropriate to occlude an aneurysm 70 of a given size so long as the length (l) is sufficient to permit the carriage 30 to expand and compress to a dimension (or width) greater than its original width. As is accepted in the art, the diameter of such an occlusion device 10 is measured in free air. The width (w) of each carriage 30 ranges (in free air) from about 2 millimeters (mm) to about 50 mm in order to be clinically practical. When deployed, the carriage 30 compresses in such a manner where the width (w) grows or expands up to about a factor of two (2) such that a carriage 30 of dimension (w) is capable of growing to approximately 2 times w (or 2w). In other words, each carriage 30 compresses like a marshmallow which causes its length (l) to be reduced and its width (w) to expand. In one embodiment, in free air, each carriage 30 can be designed in such a manner that the length (l) is greater or equal to its width (w) but in the deployed (compressed) shape, w is greater than 1. Such an occlusion device 10 comprising a compressible carriage 30 can be constructed in a variable manner so as to select the number (n) of carriages 30 as well as the length (l) and corresponding width (w) of each carriage 30 to accommodate a wide range of sizes and shapes of aneurysms 70 or body lumen to be treated. As such, in another embodiment, in free air, a carriage 30 can be designed in such a manner that its length (l) is equal to or less than its width (w) and in the deployed (compressed) shape, its width (w) remains greater than 1.

The disc-shaped resilient mesh body 20 of the continuous mesh structure extends distally from a pinch point of the opposing carriage 30 yet located medially 50 within the entire continuous mesh structure. In one embodiment, the disc-shaped mesh body 20 has a deployed shape that caves inward like a cup. The disc-shaped expansion of the mesh body 20 is the result of the body 20 having no other pinch point or pinch point-encircled marker than the medial pinch point or pinch point-encircled marker 50. Therefore, there is no pinch point or marker conforming the ends of the body into a sphere or closed, puffed shape and rather the ends of the disc-shaped body 20 extend distally and outward allowing the mesh to appose the dome of the aneurysm 70 in a low-profile manner, and effectively conform to the walls of the aneurysm 70 as the mesh disc-shaped body 20 caves inward in a cupped configuration.

For the purposes of the present invention, the terminology "low profile" means that the mesh disc-shaped body 20, in free air, has a height that is between about 10-20% of its width, and therefore in its deployed shape the resilient mesh body 20 lays flush, in a flattened manner, up against the aneurysm 70 walls. In this manner, the disc-shaped body 20 of the device 10 disclosed herein is lower and/or slimmer than typical occlusion devices readily available in the art which expand to fill the space of the aneurysm dome (fully and/or partially with respect to the majority of the space in the aneurysm) and which expand radially and/or which expand in a spherical manner. In one embodiment, the resilient mesh disc-shaped body 20, in free air, has a height between about 12-18% of its width. In another embodiment, the resilient disc-shaped body 20, in free air, has a height between about 14-16% of its width. In another embodiment, the resilient mesh disc-shaped body 20, in free air, has a height of about 15% of its width.

Figure 3:
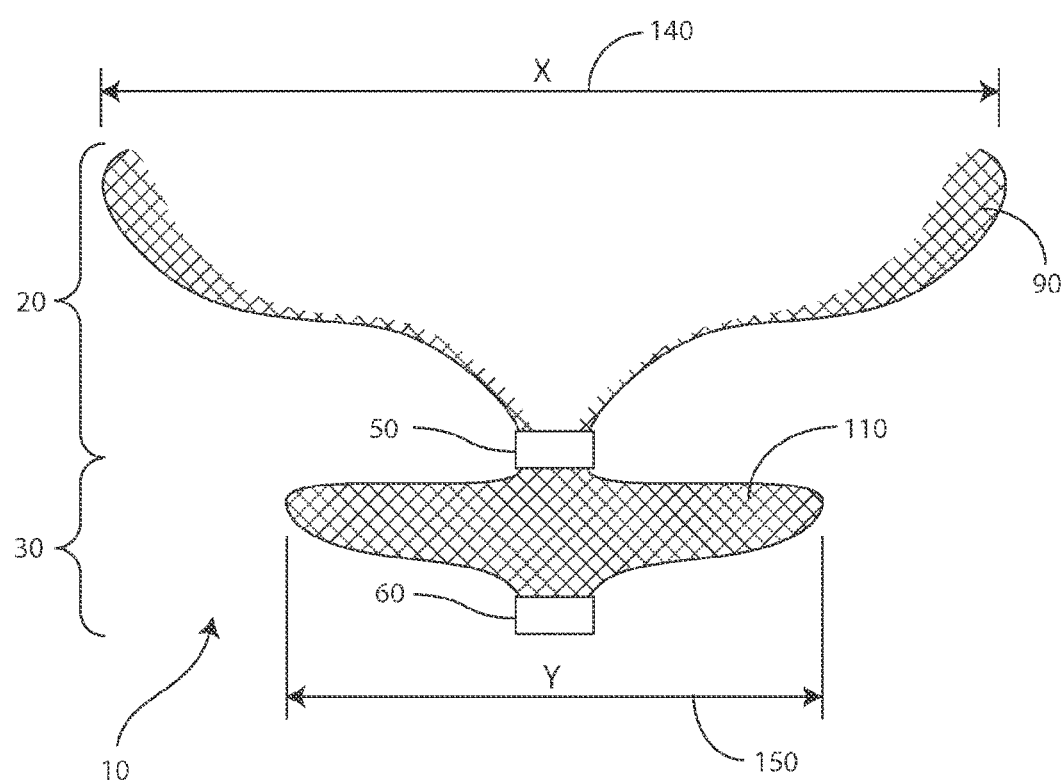
FIG. 3 illustrates an embodiment of the occlusion device disclosed herein showing the length (x) of the resilient mesh disc-shaped body is greater than the length (y) of the compressible mesh carriage in free air.

In another embodiment, as shown in FIG. 3, the low profile, disc-shaped body 20 is a single layer of resilient mesh material. In another embodiment, as shown in FIG. 1, the low profile, disc-shaped body 20 is a dual (or double) layer 40 of resilient mesh material. As such, the resilient mesh body confer its capabilities for conforming to the inner surface of the walls of the aneurysm 70 (via the opposing pressure of the protruding body 90 against the aneurysm walls) thereby providing a stabilizing effect for anchoring the device 10 in the aneurysm 70 (and thereby minimizing the need for anti-coagulation therapy and lessening the risk of clot emboli formation which could flow deeper into the vascular tree inducing stroke). Such a low profile configuration facilitates blood stasis 80, clot formation 120 and/or healing and/or shrinkage of the aneurysm 70 which is particularly advantageous if the size or mass of the aneurysm 70 is causing pain or other side effects within the patient. Moreover, such an occlusion device 10 is well suited for conformability across a broad range of aneurysm morphologies, particularly since it is well known and generally accepted that aneurysms are not perfectly round in shape.

In another embodiment, a dual layer 40 disc-shaped body 20 of an occlusion device 10 disclosed herein is a configuration of wire mesh which is folded circumferentially (circumferential fold line) and therefore doubled back on itself. The dual or doubled back layers 40 continuously intersect with the mesh pinch point or pinch point-encircled marker 50 of the compressible carriage 30. This intersection of the mesh of the disproportionate configurations of the device 10 is located at a medial pinch point 50 defining one axial end of the compressing carriage 30 and the proximal central portion of the disc-shaped mesh body 20. This medial pinch point 50 is approximately the core of the entire continuous structure of the occlusion device 10. Without wishing to be bound by theory, this doubled back or dual layer 40 of wire mesh material triggers a mechanism of action believed to contribute to the enhanced acute thrombogenicity 120 of the device 10 in animal studies. It is believed that the localizing of a small volume of clot between the dual/double layers 40, which have a high surface area contribution from the wire strands, facilitates blood stasis 80, and nucleating and stabilizing thrombus 120. In the deployed shape, the disc-shaped body 20 having a folded back dual layer 40 is deeper when compared to a non-deployed dual layer occlusion device accounting for a change in width of approximately 15% which translates to an increase in the diameter of the body when pressure is applied at the pinch point or marker 50, 60. This change in width/increase in diameter contributes to an effective anchoring effect of the deployed device 10 as blood applies pressure to the protruding mesh body 90 distributed along the aneurysm 70 walls. Such a configuration also provides sufficient apposition of the protruding body 90 of the device 10 against the aneurysm 70 wall or vessel wall for peripheral arterial or venous occlusion. Based on animal studies, such a disc-shaped body 20 provides sufficient mesh density to confer stasis 80 acutely. It is further known, based on analyzing such a body configuration in post-deployment that the wire mesh/braid distribution remains relatively uniform.

In another embodiment of the occlusion device disclosed herein, a compressible axial mesh carriage 30 comprises a coaxial inner mesh carriage. Such a coaxial mesh inner carnage creates greater flow disruption 130 and compartmentalization 100 than an axial mesh carriage without a coaxial mesh inner carriage, thereby triggering enhanced stasis 80 and thrombus 120 stabilization. In another embodiment, the axial carriage 30 and the coaxial carriage (or carriages) are constructed of dissimilar metal mesh. In a further embodiment, the dissimilar metal mesh creates a galvanic effect which can further enhance thrombus 120 development. In another further embodiment, the dissimilar metal mesh can be comprised of one metal in one carriage which possesses radiopaque properties relative to the metal in the other carnage and thus enhances visualization of the device. In such embodiments, braid mesh density can be the same or different in axial outer carriages 30 and coaxial inner carriages and wires of the inner and outer mesh can have different numbers of strands and wire diameters. Such a coaxial carriage or coaxial carriages are variable in dimension compared to the outer axial carriage 30. For example, in one embodiment, a coaxial carriage or carriages can range from about 5% to about 95% of the dimensions of the outer axial carriage of which the coaxial carriage or coaxial carriages is/are comprised within.

In one embodiment, the device 10 is constructed of a metal braid of readily available material such as, without limitation, nitinol (NiTi), cobalt chrome (CoCr) alloy, stainless steel, tungsten iridium alloy or a combination thereof. For example, the mesh of the continuous mesh structure is woven with the most clinically relevant and practical braided mesh in a range of as few as 36 braids to as many as 144 braids. In another embodiment, the angle of the weave of the metal braid construction creates the softest compressible mesh design. For example, the mesh is braided with a wire diameter of about 0.0075 inches up to about 0.005 inches. Prior to use of such an occlusion device 10, a clinician or physician determines the size and shape of the aneurysm 70 or body lumen to be treated using readily available diagnostic techniques. The physician or clinician is then able to best choose the occlusion device having a dimension or dimensions which corresponds to the given aneurysm 70 or body lumen to be treated.

"Markers" 50, 60 are well known and readily available in the medical device art. In some embodiments, a marker 50, 60 consists of metallic material, often radiopaque material, and takes the form of a shape such as a band-shaped marker, a ring-shaped marker, a tube-shaped marker, and the like, so as to encircle a pinch point of mesh of continuous mesh structure of the occlusion device 10 disclosed herein. Alternatively, a marker 50, 60 may consist of wire strands wound around and therefore encircling a given pinch point. In one embodiment, the marker or markers 50, 60 which encircle each pinch point provide positional reference under X-Ray as to where the device 10 is located in the catheter (or microcatheter) and where the device 10 is located once deployed in an aneurysm 70 or body lumen.

In one embodiment, a marker 50, 60 such as a ring encircles the pinch points defining each axial end of the compressible carriage 30 of the continuous mesh structure. As such, the marker 50, 60 of the occlusion device 10 disclosed herein is a substantially solid collar or rigid member such as, without limitation a solid ring or band comprised of materials such as, without limitation, gold, platinum, stainless steel, and/or combinations thereof. In another embodiment, radiopaque materials such as, without limitation, gold, platinum, platinum/iridium alloy, and/or combinations thereof, can be used. Such a marker 50, 60 provides positional visualization of the device during delivery and placement. The markers 50, 60 are located on the occlusion device 10 encircling pinch points on each axial end of the carriage 30. In this manner, the marker located at the distal axial end of the carriage 30 is capable of resting above or within the neck of an aneurysm 70. The solidness of the markers 50, 60 help confer stability of the device 10 within the aneurysm 70 and prevents movement or the transfer of forces through the compressible mesh carriage 30 and resilient mesh disc-shaped body 20 thereby preventing misplacement or accidental movement of the device 10. The markers 50, 60 are also configured with a junction to cooperate and release from/attach to a corresponding delivery means such as, without limitation, a delivery catheter or guide wire and/or pusher wire technologies. It also advantageously provides for full retrievability of the device 10 disclosed herein.

In another embodiment, the substantially solid marker 50, 60 comprises a radiopaque material (such as for example, without limitation, platinum, gold, platinum/iridium alloy, and/or combinations thereof) to facilitate visualization of the occlusion device 10 under fluoroscopy during delivery, placement and/or deployment. The marker 50, 60 comprises a proximal end and a distal end. Occlusion devices 10 disclosed herein may be configured to incorporate the use of markers 50, 60 to influence shape, diameter, and/or curvature of the compressible carriage 30 upon expansion during deployment. Additionally, the marker 50, 60 may be designed in various shapes to influence the overall profile of the occlusion device 10 to ensure a proper fit of the expanded/deployed occlusion device 10 within the aneurysm sac 70.

Without wishing to be bound by theory, this configuration of a continuous compressible mesh structure divided into disproportionate mesh segments triggers a mechanism of action believed to contribute to enhanced acute thrombogenicity 120 of the device in animal studies. It is also believed that the localizing of a small volume of clot between the disc-shaped mesh dual-layers 40 and basket 30 compartments, which have a high surface area contribution from the wire strands, facilitates nucleating and stabilizing thrombus 120 in an aneurysm 70. This compartmentalization 100 of the occlusion device in its deployed shape is an effective stabilizing or anchoring feature of the deployed device 10 as blood applies pressure to the mesh structure distributed across or within the neck of the aneurysm 70. Such a configuration also provides sufficient apposition of the compressible device against the aneurysm 70 wall or vessel wall for peripheral arterial or venous occlusion. The device 10 disclosed herein provides sufficient mesh density to confer stasis 80 acutely and the wire mesh/braid distribution remains relatively uniform in deployment.

In another embodiment of an occlusion device disclosed herein, the occlusion device 10 is constructed or partially constructed with a relatively uniform distribution of wire mesh strands or braids such as, without limitation, a 72 NiTi wire mesh strand braided configuration or a combination of 72 NiTi and CoCr wire mesh strand braided configuration. In other embodiments, the occlusion device 10 comprises or partially comprises wire mesh strands or braids that range from 36 to 144 NiTi strand braided configuration.

For the purposes of the present invention, the terminology "mesh density" means the level of porosity or the ratio of metal to open area of the mesh device. Mesh density relates to the number and size of the openings or pores of the mesh and by the extent that the pores are open or closed in situations where opening or pore openness varies between delivery and deployment. Generally, a high mesh density region of a resilient mesh material has approximately about 70% or more metal area and about 60% or less open area.

In one embodiment, the continuous mesh structure has or partially has an "open mesh density" for enhanced tissue integration and/or stabilization of the occlusion device. Open mesh density is greater than about 40% open area in the mesh. Open mesh density is known to have a low number, usually between about 40 and 80, picks per inch (PPI) to represent the porosity of the mesh layers. PPI is the number of repeat cross overs of braiding material in a linear inch. A high number of repeats (or PPI), usually between about 100 and 180, is an indicator that the mesh is dense. A lower number of repeats (or PPI) is an indicator that the mesh is porous (open). In an additional embodiment, the continuous mesh structure is constructed from or partially constructed from a super elastic material, such as, without limitation, nitinol. In yet another embodiment, the structure is constructed or partially constructed from DFT platinum core nitinol. In other embodiments, when the structure is partially constructed of nitinol and partially constructed of DFT platinum core nitinol. DFT platinum core nitinol is used for enhancing visualization of the device during deployment and implantation.

Figure 4:
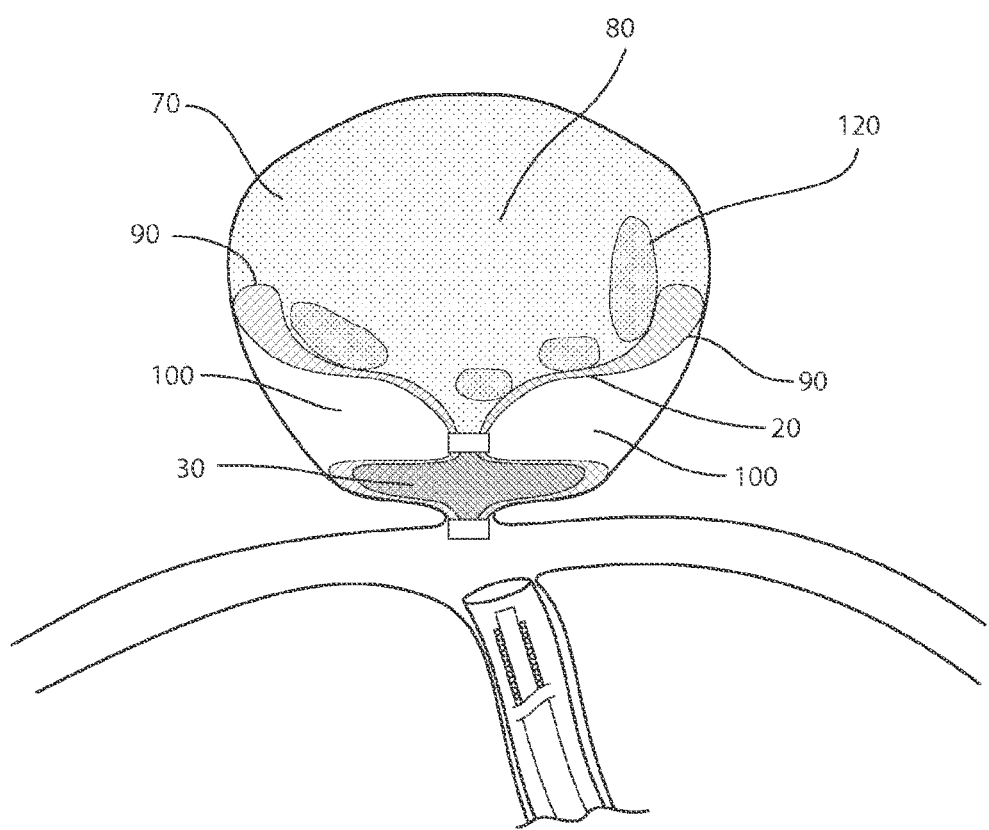
FIG. 4 illustrates the delivery of an embodiment of the occlusion device disclosed herein.

In one embodiment, as shown in FIG. 4, the occlusion device 10 disclosed herein is delivered to an aneurysm 70 or lumen via electrolytic delivery and/or deployment and/or detachment of the occlusion device 10 disclosed herein through an artery and/or vessel adjacent to the aneurysm 70 or body lumen. Electrolytic detachment means and methods such as those disclosed in U.S. Pat. No. 5,122,136 are well known in the art. In one embodiment, a coil-wound core wire (or guide wire or pusher wire) of the catheter (or micro-catheter) is attached inside the marker 60 at its most distal end to the occlusion device 10 disclosed herein. The coil wind maintains a constant diameter (d)) so as not to impact upon flexibility or stiffness of the delivery catheter or micro-catheter or guide wire. In certain embodiments, FEP (Fluorinated Ethylene Propylene) heat shrink tubing encases the coil-wound portion of the core wire. Numerous readily available and well known attachment techniques in the medical device arts can be used to attach the distal end of the core wire inside the marker 60 and to the occlusion device 10 or implant. Such attachment techniques include, without limitation, adhesives, laser melting, laser tack, spot, and/or continuous welding. In one embodiment, an adhesive is used to attach the distal end of the core wire inside the marker 60. In a further embodiment, the adhesive is an epoxy material which is cured or hardened through the application of heat or UV (ultra-violet) radiation. In an even further embodiment, the epoxy is a thermal cured, two-part epoxy such as EPO-TEK® 353ND-4 available from Epoxy Technology, Inc., 14 Fortune Drive, Billerica, Mass. Such an adhesive or epoxy material encapsulates the junction of the core wire inside the marker 60 and increases its mechanical stability.

In another embodiment, during and/or after deployment of the device 10, the coil-wound core wire detaches the occlusion device 10 disclosed herein at an electrolytic detachment site (or zone) on the core wire itself in such a manner so that the core wire is severed and/or dissolved through electrolytic action at the base of the marker 60. Such action then releases and/or places the occlusion device 10 into an aneurysm 70 or vessel to be treated.

In certain embodiments, the compressible mesh structure of the occlusion device 10 disclosed herein can be filled with an embolic material to promote clotting and closure of the aneurysm 70.

In other embodiments, the occlusion device 10 disclosed herein may further incorporate adjunctive elements and/or members such as coiling techniques, framing coils, embolic agents, additional markers, polymers, resorbent polymers and/or a combination thereof.

Resilient and compressible mesh materials for design and/or manufacture of occlusion devices are readily available and well known by those skilled in the relevant art. As such, resilient and compressible mesh materials range from a wide variety of available materials such as, without limitation, nickel titanium (nitinol or otherwise known as NiTi), stainless steel, polymers, and/or combinations thereof. Exemplary known biomedical polymeric families include, without limitation, polymers such as polyphosphazenes, polyanhydrides, polyacetals, poly (ortho esters), polyphosphoesters, polycaprolactones, polyurethanes, polylactides, polycarbonates, polyamides, and/or a combination thereof. (See, e.g., J Polym Sci B Polym Phys. Author manuscript; available in PMC 2012 Jun. 15.)

In one exemplary embodiment, the resilient and compressible mesh material is formed of woven strands of polymer material, such as, without limitation, nylon, polypropylene or polyester. The polymer strands can be filled with a radiopaque material which allows the physician treating the aneurysm to fluoroscopically visualize the location of the device within the vasculature. Radiopaque filler materials preferably include bismuth trioxide, tungsten, titanium dioxide or barium sulfate, or radiopaque dyes such as iodine. The resilient and compressible mesh material can be formed by strands of radiopaque material. The radiopaque strands allow the physician and/or radiologist to fluoroscopically visualize the location of the mesh, without the use of filled polymer materials. Such radiopaque strands may be formed with materials such as, without limitation, gold, platinum, a platinum/iridium alloy, and/or a combination thereof. In one embodiment, the resilient mesh material is constructed of 10%-45% platinum core NiTi. In another embodiment, the resilient mesh material is constructed of 10% platinum core NiTi, 15% platinum core NiTi, 20% platinum core NiTi, or 45% platinum core NiTi. 10% platinum core NiTi construction is sufficient to provide a ghost image of the occlusion device under x-ray.

Such constructed combination wires or composite wires having a radiopaque core and non-radiopaque outer layer or casing are readily available and well known in the medical device and metallic arts as DFT® (drawn-filled-tube) wires, cables or ribbons. DFT® wire is a metal-to-metal composite constructed to combine the desired physical and mechanical attributes of two or more materials into a single wire. By placing the more radiopaque, but more ductile material in the core of the wire, the NiTi outer layer is able to provide the resulting composite wire with similar mechanical properties of a 100% NiTi wire. DFT® wires are available from Fort Wayne Metals Corp., Fort Wayne, Ind., U.S.A. See also, for example, the journal article entitled Biocompatible Wire by Schaffer in Advanced Materials & Processes, October 2002, pages 51-54, incorporated herein by reference.

Where the compressible mesh structure is formed of radiopaque metal strands, the strands may be covered with a polymer coating or extrusion. The coating or extrusion over the radiopaque wire strands provides fluoroscopic visualization but also increases the resistance of the strands to bending fatigue and may also increase lubricity of the strands. The polymer coating or extrusion, in one embodiment, is coated or treated with an agent which tends to resist clotting, such as heparin. Such clot resistant coatings are generally known. The polymer coating or extrusion can be any suitable extrudable polymer, or any polymer that can be applied in a thin coating, such as Teflon® or polyurethane.

In yet another embodiment, the strands of the compressible mesh structure are formed using both metal and polymer braided strands. Combining the metal strands with the polymer strands into a braid changes the flexibility characteristics of mesh. The force required to deploy and/or collapse such a mesh portion is significantly reduced over that required for a mesh portion that includes only metal mesh strands. However, the radiopaque characteristics of the mesh for fluoroscopic visualization are retained. Metal strands forming such a device includes, without limitation, stainless steel, gold, platinum, platinum/iridium, nitinol, and/or combinations thereof. Polymer strands forming the device can include nylon, polypropylene, polyester, Teflon®, and/or combinations thereof. Further, polymer strands of the mesh material can be chemically modified to make them radiopaque with known techniques such as, without limitation, by using gold deposition onto the polymer strands, or by using ion beam plasma deposition of suitable metal ions onto the polymer strands.

The compressible mesh structure can also be formed with filaments or strands of varying diameter and/or varying flexibility. For example, wire diameters for use in the occlusion device disclosed herein range from about 0.0075 inches up to about 0.005 inches. By varying the size or flexibility of the polymer strands, the flexibility characteristics of the mesh, upon deployment, can also be varied. By varying the flexibility characteristics, both the deployed (compressed) and delivery (constrained) configuration of the resilient and compressible mesh structure can be varied or changed to substantially any desired shape.

Not only can the mesh be formed of both polymer strands or filaments and metal strands or filaments, but it can be formed using filaments of different polymer materials. For example, different polymer materials having different flexibility characteristics can be used in forming the mesh. This alters the flexibility characteristics to change the resultant configuration of the mesh structure in both the deployed and the collapsed positions. Such biomedical polymers are readily known and available in the art and can be derived from polymeric families such as, without limitation, polyphosphazenes, polyanhydrides, polyacetals, poly (ortho esters), polyphosphoesters, polycaprolactones, polyurethanes, polylactides, polycarbonates, polyamides, and/or a combination thereof.

Compressible mesh materials suitable for use within the mesh carriages may take the form of a flat woven sheet, knitted sheet, or a laser cut wire mesh. In general, the material should include two or more sets of substantially parallel strands, with one set of parallel strands being at a pitch of between 45 degrees and 135 degrees with respect to the other set of parallel strands. In some embodiments, the two sets of parallel strands forming the mesh material are substantially perpendicular to each other. The pitch and general construction of the mesh material may be optimized to meet the performance needs of the occlusion device 10.

The wire strands of the metal fabric used in the occlusion device 10 disclosed herein should be formed of a material which is both resilient and compressible and can be heat-treated to substantially set a desired shape. Materials which are believed to be suitable for this purpose include a cobalt-based low thermal expansion alloy referred to in the field of occlusion devices as Elgiloy®, nickel-based high-temperature high-strength "superalloys" commercially available from Haynes International under the trade name Hastelloy®, nickel-based heat treatable alloys sold under the name Incoloy® by International Nickel, and a number of different grades of stainless steel. The important factor in choosing a suitable material for the wires is that the wires retain a suitable amount of the deformation induced by the molding surface (or shape memory, as described below) when subjected to a predetermined heat treatment.

One class of materials which meet these qualifications are so-called shape memory alloys. Such alloys tend to have a temperature induced phase change which will cause the material to have a preferred configuration which can be fixed by heating the material above a certain transition temperature to induce a change in the phase of the material. When the alloy is cooled, the alloy will "remember" the shape it was in during the heat treatment and will tend to assume that same and/or similar configuration unless constrained from doing so.

One particular shape memory alloy for use in the occlusion device 10 disclosed herein is nitinol, an approximately stoichiometric alloy of nickel and titanium, which may also include other minor amounts of other metals to achieve desired properties. NiTi alloys such as nitinol, including appropriate compositions and handling requirements, are well known in the art and such alloys need not be discussed in detail here. For example, U.S. Pat. Nos. 5,067,489 and 4,991,602, the teachings of which are incorporated herein by reference, discuss the use of shape memory NiTi alloys in guide wire-based technologies. Such NiTi alloys are preferred, at least in part, because they are commercially available and more is known about handling such alloys than other known shape memory alloys. NiTi alloys are also very elastic. Indeed, they are said to be known as "superelastic" or "pseudoelastic." This elasticity will help an occlusion device 10 as disclosed herein return to prior expanded configuration for deployment thereof.

The wire strands can comprise a standard monofilament of the selected material, i.e., a standard wire stock may be used. In some embodiments, 72 wire strands and/or 72 strand braid configuration is used. In other embodiments, the occlusion device comprises wire mesh strands or braids that range from 36 to 144 NiTi strand braided configurations. If so desired, though, the individual wire strands may be formed from "cables" made up of a plurality of individual wires. For example, cables formed of metal wires where several wires are helically wrapped about a central wire are commercially available and NiTi cables having an outer diameter of 0.003 inches or less can be purchased. One advantage of certain cables is that they tend to be "softer" than the monofilament wires having the same diameter and formed of same material. Additionally, the use of a cable can increase the effective surface area of the wire strand, which will tend to promote thrombosis 120.

An occlusion device 10 disclosed herein is configured with a continuous mesh structure having a mesh density sufficient for functioning in such a manner as an endothelial cell scaffold layers or compartments 100 filling a vessel or body lumen or aneurysm 70 and thereby reducing blood flow 130 by about 60% to trigger clot formation and/or healing of the aneurysm 70 and/or ultimate stasis 80. For the purposes of the occlusion device 10 disclosed herein, the terminology "mesh density" means the level of porosity or the ratio of metal to open area of the mesh structure. Mesh density relates to the number and size of the openings or pores of the mesh and by the extent that the pores are open or closed in situations where opening or pore openness varies between delivery and deployment. Generally, a high mesh density region of a resilient mesh material has approximately about 40% or more metal area and about 60% or less open area.

In some embodiments, the compressible mesh structure may be formed uniformly of the same material, however such material may have different knitted, stitched, braided, and/or cut construction.

In other embodiments, the implantable occlusion device 10 disclosed herein can be used for the process of peripheral vascular embolization (a process well known in the art and known to involve the shutdown of blood flow 130 distal to a specified vascular point), for example, in the treatment and/or amelioration of peripheral arterial or venous pathologies and/or any related pathologies requiring vessel occlusion for the treatment thereof.

The occlusion device 10 of the invention disclosed herein may incorporate reasonable design parameters, features, modifications, advantages, and variations that are readily apparent to those skilled in the art in the field of occlusion devices.

EXAMPLES

A study protocol with respect to the occlusion device 10 disclosed herein and justification for animal use will be reviewed and approved by the Institutional Animal Care and Use Committee (IACUC) at ISIS Services and the procedures carried out under veterinarian supervision.

The rabbit elastase aneurysm model is a well-accepted and art-recognized model for testing novel neurointerventional devices and has been the subject of a number of clinical publications regarding efficacy and similarity to human response. (See, e.g., Altes et al. Creation of Saccular Aneurysms in the Rabbit: A Model Suitable for Testing Endovascular Devices. AJR 2000; 174: 349-354.) It therefore is readily accepted by the regulatory agencies as an appropriate test model. The model's coagulation system is highly similar to that of humans. In addition, the model has advantageous anatomical aspects in that the diameters of the rabbits' extra-cranial carotid arteries are highly similar to the diameter of extra-cranial carotid arteries in humans. Moreover, elastase-induced aneurysms have been shown to behave in a histologically similar manner as human aneurysms.

A number of embodiments of the invention have been described. Without departing from the scope and spirit of the occlusion device 10 disclosed herein, reasonable features, modifications, advantages, and design variations of the claimed apparatus will become readily apparent to those skilled in the art by following the guidelines set forth in the preceding detailed description and embodiments. Accordingly, other embodiments are within the scope of the following claims.

What is claimed is:

1. An occlusion device having a continuous mesh structure comprising:
   a resilient mesh disc-shaped body extending distally and outward from a medial pinch point, wherein the resilient mesh disc-shaped body has an exposed internal surface that has a convex portion adjacent the medial pinch point, followed distally by a concave portion that is followed by a distal end of the resilient mesh disc-shaped body; and
   a compressible mesh carriage extending proximally from the medial pinch point.

2. The occlusion device of claim 1, wherein a marker encircles the medial pinch point of the continuous mesh structure.

3. The occlusion device of claim 2, wherein the marker is a solid ring or band.

4. The occlusion device of claim 1, wherein a marker encircles a non-medial pinch point of the compressible mesh carriage.

5. The occlusion device of claim 4, wherein the marker encircling the non-medial pinch point of the compressible mesh carriage is a detachment junction to deploy the occlusion device and/or an attachment junction to retrieve the occlusion device.

6. The occlusion device of claim 1, wherein the resilient mesh disc-shaped body of the occlusion device is a dual or double layer mesh.

7. The occlusion device of claim 6, wherein the dual or double layer mesh comprises a single layer of mesh folded circumferentially.

8. The occlusion device of claim 7, wherein the dual or double layer continuously intersects with the medial pinch point.

9. The occlusion device of claim 1, wherein the medial pinch point defines a proximal central portion of the resilient mesh disc-shaped body.

10. The occlusion device of claim 1, wherein the resilient mesh disc-shaped body, in free air, has a height that is between 10-20% of its width.

11. The occlusion device of claim 1, wherein the continuous mesh structure is configured to expand to a deployed shape to fill a body lumen or aneurysm.

12. The occlusion device of claim 1, wherein the continuous mesh structure has an open mesh density for enhanced tissue integration and/or stabilization of the occlusion device.

13. A kit for treatment and/or amelioration of an aneurysm, the kit comprising
the occlusion device of claim 1; and
a delivery system or detachment system corresponding to the occlusion device.

14. The kit of claim 13, wherein the delivery system is a microcatheter, catheter, guide wire, or pusher wire.

15. The kit of claim 13, wherein the detachment system is an electrolytic detachment system.

16. A method for treating or ameliorating an aneurysm in a patient, the method comprising:
delivering the occlusion device of claim 1 to the aneurysm; and
deploying the occlusion device in the aneurysm, thereby treating or ameliorating the aneurysm in the patient.

* * * * *